(12) United States Patent
Popwell et al.

(10) Patent No.: US 12,702,588 B2
(45) Date of Patent: Aug. 11, 2026

(54) CONTACT LENS PACKAGES HAVING TWISTING OR THIMBLE LEVERS AND METHODS OF HANDLING

(71) Applicant: JOHNSON & JOHNSON VISION CARE, INC., Jacksonville, FL (US)

(72) Inventors: Sam Jonathan Popwell, Jacksonville, FL (US); Daniel Graham Ward, Cambridge (GB); Stephen Sams, Cambridge (GB); William Stephen Honey, Bath (GB)

(73) Assignee: JOHNSON & JOHNSON VISION CARE, INC., Jacksonville, FL (US)

(*) Notice: Subject to any disclaimer, the term of this patent is extended or adjusted under 35 U.S.C. 154(b) by 0 days.

(21) Appl. No.: 18/719,438

(22) PCT Filed: Dec. 13, 2022

(86) PCT No.: PCT/IB2022/062150
§ 371 (c)(1),
(2) Date: Jun. 13, 2024

(87) PCT Pub. No.: WO2023/111853
PCT Pub. Date: Jun. 22, 2023

(65) Prior Publication Data

US 2025/0041114 A1 Feb. 6, 2025

Related U.S. Application Data

(60) Provisional application No. 63/289,427, filed on Dec. 14, 2021.

(51) Int. Cl.
*A61F 9/00* (2006.01)
*A45C 11/00* (2006.01)
(Continued)

(52) U.S. Cl.
CPC ........ *A61F 9/0061* (2013.01); *B65D 41/0428* (2013.01); *B65D 41/0485* (2013.01); *B65D 51/26* (2013.01); *B65D 2585/545* (2013.01)

(58) Field of Classification Search
CPC ................ A45C 11/005; A45C 11/046; A45C 2011/007; A61F 9/0061; A61F 9/00;
(Continued)

(56) References Cited

U.S. PATENT DOCUMENTS 3,088,830 A 5/1963 Graham
3,089,500 A 5/1963 Stalcup
(Continued)

FOREIGN PATENT DOCUMENTS

BR 202016013147 4/2019
CN 101484037 A 7/2009
(Continued)

OTHER PUBLICATIONS

International Search Report & Written Opinion, International Patent Application No. PCT/IB2022/062150, dated Mar. 16, 2023, 8 pages.
(Continued)

*Primary Examiner* — Gideon R Weinerth
(74) *Attorney, Agent, or Firm* — Casimir Jones, S.C.; Thomas J. Lyneis

(57) ABSTRACT

Described herein are devices and methods for storage and application of a contact lens. The device includes an applicator cap (102) including a handle portion (**106*a*) having a first end, a second end, and a body that extends between the first end and the second end. The body includes at least one lever surface. The device includes a container (104**) having a reservoir configured to house a contact lens and packaging solution. The at least one lever surface is configured to provide at least one leverage point for movement of the applicator cap relative to the container.

27 Claims, 14 Drawing Sheets

(51) Int. Cl.
*B65D 41/04* (2006.01)
*B65D 51/26* (2006.01)

(58) Field of Classification Search
CPC .............. A61F 2/0095; B65D 41/0428; B65D 41/0485; B65D 51/26; B65D 2585/545; B65D 81/22; B65D 2251/02; Y10S 134/901; Y10S 294/902; A61L 12/00
USPC ............................ 206/5.1; 294/1.2; 606/107
See application file for complete search history.

(56) References Cited

U.S. PATENT DOCUMENTS 3,159,308 A 12/1964 Lawrence
3,344,461 A * 10/1967 Floor .................. G02C 13/008 15/118
3,369,656 A 2/1968 Skinner
3,414,117 A 12/1968 Leeds
3,473,886 A 10/1969 Leeds
3,490,806 A 1/1970 Lopez-Calleja
3,524,455 A 8/1970 Hoogesteger
3,584,908 A 6/1971 Ray
3,804,236 A * 4/1974 Tanaka ................ A45C 11/005 206/205
3,977,517 A 8/1976 Kadlecik et al.
4,093,291 A * 6/1978 Schurgin .............. A61F 9/0061 294/1.2
4,167,283 A * 9/1979 Feldman .............. A61F 9/0061 294/25
4,187,574 A 2/1980 Wrue
D261,896 S * 11/1981 Schurgin ..................... D16/331
4,392,569 A 7/1983 Shoup
4,415,076 A 11/1983 Campbell
4,444,307 A 4/1984 Jermyn
4,495,313 A 1/1985 Larsen
4,512,601 A 4/1985 Jacobstein
4,512,602 A * 4/1985 England ............... A61F 9/0061 294/1.2
4,659,782 A 4/1987 Spinelli
4,659,783 A 4/1987 Spinelli
4,691,820 A 9/1987 Martinez
4,889,664 A 12/1989 Kindt-Larsen et al.
4,942,959 A 7/1990 Sauber
4,986,414 A 1/1991 Ashley et al.
5,031,622 A 7/1991 Lahaye
5,039,459 A 8/1991 Kindt-Larsen et al.
5,053,208 A 10/1991 Seamons
5,069,494 A * 12/1991 Reinson .............. A45C 11/005 294/187
5,099,987 A 3/1992 Bieri
5,227,039 A 7/1993 Pankow
5,244,981 A 9/1993 Seidner et al.
5,246,259 A * 9/1993 Hellenkamp ......... A61F 9/0061 294/1.2
5,314,960 A 5/1994 Spinelli
5,331,067 A 7/1994 Seidner et al.
5,371,147 A 12/1994 Spinelli
5,375,698 A 12/1994 Eward et al.
5,407,062 A 4/1995 Shannon
5,415,275 A 5/1995 Girimont
5,431,879 A * 7/1995 Heyl ........................ A61L 2/18 422/312
5,452,027 A 9/1995 Tylec
5,474,169 A 12/1995 Bauman
5,496,084 A * 3/1996 Miralles Medan ... A61F 9/0061 606/210
5,515,964 A 5/1996 Bauman
5,609,246 A 3/1997 Borghorst et al.
5,620,088 A 4/1997 Martin
5,695,049 A 12/1997 Bauman
5,704,468 A 1/1998 Lust et al.
5,711,416 A 1/1998 Bauman
5,722,536 A 3/1998 Pierce
5,732,990 A 3/1998 Yavitz
5,760,100 A 6/1998 Nicolson et al.
5,776,999 A 7/1998 Nicolson et al.
5,785,370 A * 7/1998 Pomerantz ............ A61F 9/0061 294/187
5,789,461 A 8/1998 Nicolson et al.
5,849,811 A 12/1998 Nicolson et al.
5,853,085 A 12/1998 Luttrell
5,879,038 A * 3/1999 Morgan ................ A61F 9/0061 294/187
5,941,583 A * 8/1999 Raimondi ............ A61F 9/0061 294/187
5,965,631 A 10/1999 Nicolson et al.
5,998,498 A 12/1999 Vanderlaan
6,010,001 A 1/2000 Osborn, III
6,087,415 A 7/2000 Vanderlaan
6,138,212 A 10/2000 Cummings
6,138,312 A 10/2000 Cummings
6,253,912 B1 7/2001 Oneill
6,260,695 B1 7/2001 Tasber
6,276,797 B1 8/2001 Shannon
6,280,530 B1 8/2001 Pankow
6,286,666 B1 9/2001 Umdasch
6,289,907 B1 9/2001 Horian et al.
RE37,558 E 2/2002 Abrams
6,367,929 B1 4/2002 Maiden et al.
6,401,915 B1 6/2002 Faxe
6,572,165 B2 6/2003 Faxe
6,822,016 B2 11/2004 Mccabe et al.
6,867,245 B2 3/2005 Iwata et al.
6,943,203 B2 9/2005 Vanderlaan
7,086,526 B2 8/2006 Newman
7,225,919 B2 6/2007 Hamilton
7,247,692 B2 7/2007 Laredo
7,249,848 B2 7/2007 Laredo
7,275,275 B2 10/2007 Pankow
7,347,466 B1 * 3/2008 Feldman .............. A61F 9/0061 623/6.11
7,398,877 B1 7/2008 Nelson
7,410,050 B2 8/2008 Py
7,426,993 B2 9/2008 Coldrey
7,441,650 B2 10/2008 Tanaka
7,461,740 B2 12/2008 Newman
7,540,376 B2 6/2009 Mahieu
7,553,880 B2 6/2009 Nicolson et al.
7,666,921 B2 2/2010 Mccabe et al.
7,786,185 B2 8/2010 Rathore
7,819,241 B2 10/2010 Post-Smith
7,832,551 B2 11/2010 Newman
7,832,552 B2 11/2010 Newman
7,850,002 B2 12/2010 Newman
7,938,255 B2 5/2011 Newman
7,956,131 B2 6/2011 Arnold
8,022,158 B2 9/2011 Rathore
8,104,608 B2 1/2012 Newman
D658,077 S 4/2012 Newman
8,251,205 B2 8/2012 Azera
8,273,802 B2 9/2012 Laredo
8,399,538 B2 3/2013 Steffan
8,450,387 B2 5/2013 Mccabe et al.
8,470,906 B2 6/2013 Rathore
8,487,058 B2 7/2013 Liu
8,507,577 B2 8/2013 Zanini
D690,207 S 9/2013 Newman
8,637,621 B2 1/2014 Iwata et al.
8,703,891 B2 4/2014 Broad
8,833,548 B2 9/2014 Hsieh
8,881,892 B1 11/2014 Linhardt
8,937,110 B2 1/2015 Alli
8,937,111 B2 1/2015 Alli
8,940,812 B2 1/2015 Reboul
9,044,075 B2 6/2015 Linhardt
9,056,878 B2 6/2015 Fujisawa
9,057,821 B2 6/2015 Broad
9,067,720 B2 6/2015 Howell
9,095,195 B2 8/2015 Mori
9,125,808 B2 9/2015 Alli
9,140,825 B2 9/2015 Alli
9,156,934 B2 10/2015 Alli
9,170,349 B2 10/2015 Mahadevan

(56) References Cited

U.S. PATENT DOCUMENTS 9,206,544 B2 12/2015 Zeng
9,244,196 B2 1/2016 Scales
9,244,197 B2 1/2016 Alli
9,297,928 B2 3/2016 Molock
9,297,929 B2 3/2016 Scales
9,320,566 B1 4/2016 Alston et al.
9,358,736 B2 6/2016 Wang
9,576,609 B2 2/2017 Huang
9,668,558 B2 6/2017 Clamp
9,701,458 B2 7/2017 Barrows
D804,323 S 12/2017 Harrison
D805,920 S 12/2017 Clamp
9,839,270 B2 12/2017 Howell
D813,537 S 3/2018 Miura
10,092,075 B2 10/2018 Barre
10,138,042 B2 11/2018 Fawdington
10,194,724 B2 2/2019 Newman
10,265,214 B2 4/2019 Shulman
10,364,082 B2 7/2019 Coon
10,368,621 B2 8/2019 Barre
10,463,127 B2 11/2019 Kim
10,577,166 B2 3/2020 Barrows
10,661,964 B2 5/2020 Tokarski
D899,080 S 10/2020 Yasuda
D899,081 S 10/2020 Yamamoto
10,901,236 B2 1/2021 Schweizer
10,926,944 B2 2/2021 Huang
11,071,644 B2 7/2021 Greenwood
11,077,969 B2 8/2021 Newman
11,136,176 B2 10/2021 Almond
11,229,266 B2 1/2022 Almond et al.
11,628,998 B2 4/2023 Ho
11,649,099 B2 5/2023 Ellis
11,751,654 B2 9/2023 Lansing
2001/0017271 A1 8/2001 Yavitz
2002/0063068 A1* 5/2002 Faxe .................... A45C 11/005 294/1.2
2002/0158477 A1 10/2002 Faxe
2002/0163212 A1 11/2002 Py
2004/0134005 A1 7/2004 Pankow
2004/0238380 A1 12/2004 Newman
2005/0087453 A1 4/2005 Mahieu et al.
2005/0103649 A1 5/2005 Vulcu et al.
2005/0194798 A1* 9/2005 Wallock ................ A61F 9/0061 294/1.2
2005/0218012 A1 10/2005 Tanaka et al.
2006/0201103 A1 9/2006 Tokarski et al.
2006/0213783 A1 9/2006 Tokarski
2006/0213784 A1 9/2006 Tokarski et al.
2006/0219577 A1 10/2006 Newman
2006/0260956 A1 11/2006 Stachowski
2006/0260957 A1 11/2006 Hamilton
2007/0000792 A1 1/2007 Newman et al.
2007/0164576 A1 7/2007 Kim
2007/0199831 A1* 8/2007 Tokarski ............... A61F 9/0061 206/5.1
2008/0011619 A1 1/2008 Newman
2008/0047848 A1 2/2008 Tokarski et al.
2008/0078681 A1 4/2008 Newman
2008/0170201 A1 7/2008 Filippo
2009/0121370 A1 5/2009 Barrows
2009/0139879 A1 6/2009 Tokarski
2009/0200182 A1 8/2009 Post-Smith
2010/0048847 A1 2/2010 Broad
2010/0072082 A1 3/2010 Kang
2010/0187140 A1 7/2010 Tokarski et al.
2011/0017243 A1 1/2011 Voss
2012/0267262 A1 10/2012 Wang
2013/0082023 A1* 4/2013 Wand ................. B65D 41/0485 215/305
2013/0091613 A1 4/2013 Meltzner
2013/0277242 A1 10/2013 Mori
2014/0001059 A1 1/2014 Hsieh et al.
2014/0027462 A1 1/2014 Willat
2014/0027465 A1 1/2014 Howell et al.
2014/0246337 A1 9/2014 Newman
2014/0263317 A1* 9/2014 Linder ................. B65D 41/045 220/212.5
2015/0014187 A1 1/2015 Gilman
2015/0150346 A1 6/2015 Yasuda
2015/0173474 A1 6/2015 Barrows
2016/0198825 A1 7/2016 Fawdington
2017/0172269 A1 6/2017 Lin
2018/0134475 A1 5/2018 Newman et al.
2018/0161203 A1* 6/2018 Hopper ..................... A61F 9/00
2018/0340622 A1 11/2018 Godfrey
2018/0344520 A1* 12/2018 Daniels ................. A61F 9/0061
2019/0046353 A1 2/2019 Greenwood et al.
2019/0133275 A1 5/2019 Newman
2019/0216644 A1* 7/2019 Hershoff .............. B25J 15/0683
2019/0274879 A1* 9/2019 Omberg ................ A61F 9/0061
2020/0229560 A1 7/2020 Almond et al.
2020/0229561 A1 7/2020 Almond et al.
2020/0229562 A1 7/2020 Almond et al.
2020/0229563 A1 7/2020 Almond et al.
2020/0231342 A1* 7/2020 Ziccardi ............. B65D 41/0485
2020/0231351 A1 7/2020 Almond et al.
2020/0383440 A1 12/2020 Newman
2021/0139229 A1 5/2021 Huang
2022/0330671 A1 10/2022 Bruchon
2022/0365368 A1 11/2022 Greenwood et al.
2023/0083028 A1 3/2023 Popwell
2023/0143203 A1* 5/2023 Popwell ............. B65D 77/2024 206/5.1
2023/0276917 A1 9/2023 Popwell
2023/0278757 A1* 9/2023 Wommelsdorf ... B65D 41/3404 220/262
2025/0041114 A1* 2/2025 Popwell ................ A61F 9/0061

FOREIGN PATENT DOCUMENTS

CN 101662967 3/2010
CN 206827263 U 1/2018
CN 208610048 U 3/2019
CN 111759065 10/2020
DE 4415003 6/1995
DE 202006004323 5/2006
EP 0269367 6/1988
EP 3045071 7/2016
EP 2768465 B1 9/2019
FR 2712398 5/1995
FR 2777360 10/1999
GB 2551530 12/2017
JP H01279222 11/1989
JP H10313928 12/1998
JP 2001046134 2/2001
JP 5184925 1/2013
JP 2014218255 11/2014
JP 6004912 B2 10/2016
JP 2016179837 A 10/2016
JP 6129238 4/2017
JP 6129239 4/2017
JP 6339322 B2 5/2018
KR 100768522 10/2007
KR 20080066930 7/2008
KR 20080090252 10/2008
KR 20090060075 6/2009
KR 20100002433 A 1/2010
KR 101495874 2/2015
KR 20160064382 6/2016
KR 20190003113 12/2019
KR 200490803 2/2020
KR 102154537 B1 9/2020
NL 2000268 4/2008
TW 200930318 7/2009
TW D159617 4/2014
TW D172590 12/2015
WO WO 99/21519 5/1999
WO WO 2002088780 11/2002
WO WO 2003022321 3/2003
WO WO 2005/006062 1/2005
WO WO 2005/055760 6/2005
WO WO 2005073105 8/2005
WO WO 2005/082721 9/2005

(56) References Cited

FOREIGN PATENT DOCUMENTS

| | | |
|---|---|---|
| WO | WO 2006068583 | 6/2006 |
| WO | WO 2006105179 | 10/2006 |
| WO | WO 2008061992 | 5/2008 |
| WO | WO 2008120954 | 10/2008 |
| WO | WO 2009/059231 | 5/2009 |
| WO | WO 2009069265 | 6/2009 |
| WO | WO 2012165209 | 12/2012 |
| WO | WO 2012168964 | 12/2012 |
| WO | WO 2013058712 | 4/2013 |
| WO | WO 2013/134547 | 9/2013 |
| WO | WO 2013/136361 | 9/2013 |
| WO | WO 2013/153582 | 10/2013 |
| WO | WO 2014185354 | 11/2014 |
| WO | WO 2014195588 | 12/2014 |
| WO | WO 2015150704 | 10/2015 |
| WO | WO 2017/137738 | 8/2017 |
| WO | WO 2019013199 | 1/2019 |
| WO | WO 2020/152444 | 7/2020 |
| WO | WO 2020/152446 | 7/2020 |
| WO | WO 2021176760 | 9/2021 |
| WO | WO 2021/260353 | 12/2021 |
| WO | WO 2022/054033 | 3/2022 |
| WO | WO 2022054031 | 3/2022 |
| WO | WO 2022123525 | 6/2022 |

OTHER PUBLICATIONS

Extended European Search Report for European Application No. 22205781.2, mailed Apr. 21, 2023, 07 Pages.

International Preliminary Report on Patentability for International Application No. PCT/IB2022/062150, mailed Jun. 27, 2024, 10 Pages.

International Search Report and Written Opinion for International Application No. PCT/IB2022/062149, mailed Mar. 17, 2023, 12 Pages.

International Search Report and Written Opinion for International Application No. PCT/IB2022/062300, mailed Mar. 28, 2023, 14 Pages.

* cited by examiner

CONTACT LENS PACKAGES HAVING TWISTING OR THIMBLE LEVERS AND METHODS OF HANDLING

I. BACKGROUND OF THE INVENTION

In a conventional contact lens package, the contact lens typically sits in a molded plastic base having a cavity (or "bowl") that houses the contact lens in a concave-side-up orientation. As a result, the user experience for transferring a contact lens from the package to an eye generally involves the user "fishing" the contact lens out of the bowl with a finger and then flipping the lens so that it is in the correct orientation on the finger for placement on the eye. This process requires touching the lens multiple times, which can transfer contaminants or pathogens from the hand to the lens and ultimately to the eye. Not only is this handling experience unsanitary, but it is also unduly cumbersome, messy, and mechanically stressful to the lens, which can tear, rip, or distort when overly manipulated. While some packages have been designed to present the lens in a convex-side-up orientation to obviate the need for flipping the lens, they often still require the lens to be "fished" from the packaging solution or otherwise necessitate manipulation of the lens and/or multiple touches of the lens to achieve transfer of the lens to the eye.

In view of the growing awareness around ocular health and the customer demand for a more convenient experience, a need has arisen for contact lens packaging that enables a less messy and more sanitary contact lens handling process. In one respect, it would be ideal to provide wearers of contact lenses with a "single touch" package—that is, a package whereby the wearer of contact lenses can take the lens from the lens storage package with a single touch of one of his or her fingers, and then, with this single touch, position the lens correctly on the eye. In such a design, there would be no need for transfer and manipulation of the lens from one finger to another before placing the lens on the eye. Providing such a single touch package would not only streamline the lens preparation and insertion process; it would also diminish the possibility of dropping the lens or exposing the lens to additional bacteria on a wearer's other fingers as the lens is being prepared for orientation and insertion onto the eye, and it also reduces the possibility of touching the side of the lens which is intended to contact the eye.

Design of a single or no touch lens package faces some distinct challenges. The wearer ideally should be able to consistently position the lens to adhere to the finger during removal from the package, and then the lens needs to consistently release from the finger onto the eye. Contact lenses (of both the reusable and daily disposable variety) each has its own unique surface, bulk, and geometric properties. Finger size and the force a contact lens wearer imparts on the lens during transfer can also vary. These factors can impact the process for taking the lens from the package onto the finger and then onto the surface of the eye. Among other considerations: it would be desirable for wearers to be able to drain away any packaging solution which might impact the ability of adhering the lens to the finger, as variation in the amount of packaging solution adhering to the lens and package can impact the process of placing the lens on the finger. It would also be desirable for package solution to drain away in a controlled fashion that avoids spillage. It would also be beneficial for the packaging solution to remain sterile and accessible to the wearer after opening to permit re-wetting or cleansing of the lens. Also, the wearer may be concerned about the potential of transferring bacteria or external products such as make up to the contact lens; and of course, manufacture of the package itself should conform to expected industry standards recognized by the medical and commercial provider communities.

Further, the single or no touch package ideally should not result in an inordinate increase in the cost of goods over current contact lens packages, as this could result in increased costs to the wearer community. The package should not make it difficult to hold the lens when removed from the package. Additionally, if the configuration of the package were to maintain, or even reduce the volume of solution needed to package the lens, this would reduce the ecological impact of the lens package. Similarly, it would be beneficial if all or part of the package could be made of recycled materials, and/or recyclable in whole or part.

In addition, it would be advantageous if the package were composed of materials that are already approved by the various regulatory bodies and ideally did not require a change in solution chemistry or lens composition. Optimally, as well, the functionality of the package preferably does not incorporate any electronics or other electrical components if such components could adversely affect performance of either the package or the lens.

There are several desirable attributes that have made achieving the function of a single or no touch package challenging and that are often lacking in known attempts to create a single touch package. These attributes include, for example, the following: i) the package ideally should protect the lens, i.e., it should ensure the lens's integrity (e.g., lens shape and optical integrity), while at the same time prevent crushing or damage to the lens; ii) the lens package should maintain the hydration of the lens when stored to maintain the lens's properties; and iii) the lens in its package preferably should be configured so that when desired, it is fully submerged in the packaging solution, yet be cleared of such solution when ready to be transferred from the packaging; iv) the package generally should have a retortable seal and contain both the lens and solution; v) the package preferably should maintain the lens in the desired convex orientation to the wearer; vi) the lens should be positioned so that it can be easily removed by the wearer; and vii) the package ideally should allow the packaging solution to be effectively drained away from the lens upon opening of the packaging and prior to lens removal to enable easier transferred to the wearer's finger and then onto the eye.

Known packages that have sought to provide reduce-touch, single touch, or no touch orientations fail to provide one or more of the above-noted desired attributes for a single-touch package or no touch package. For example, WO2014/195588, WO2009/069265, JP6339322 disclose packages which present the lens in a convex, bowl down configuration. However, the lens support structures substantially match the shape of the contact lens, which provides undesirable contact area between the lens and lens support. These references are also silent as to mechanisms for effective solution drainage from the lens and lens support.

U.S. Pat. No. 10,265,214B2 discloses eye drop applicators that facilitate measurement and accurate, effective administration of a medication, such as eye drops or any type of liquid medication. However, the package does not include any mechanism for storing or retaining a contact lens.

WO1999021519A1 discloses packages arranged to, when opening the package, function as an applicator with a concave surface formed mainly complementary to the convex side of the contact lens for carrying the contact lens during application; and a second part closely joined with the first part in the unopened condition of the package and together with this first part delimiting a chamber for storing the contact lens. However, the package does not disclose a mechanism providing a lever to manipulate the cap of a package.

U.S. Pat. No. 6,572,165B2 discloses a manipulator for applying a contact lens in or removing it from a user's eye. However, the manipulator does not disclose a surface configured to rotate a cap about an axis.

U.S. Pat. No. 5,941,583A discloses a contact lens insertion and manipulation assembly. The manipulator device allows the user to remove the contact lens from the storage container without the user touching the contact lens. However, the insertion and manipulation assembly does not disclose a curved or surface configured to rotate a cap about an axis.

The foregoing noted deficiencies of the prior art are merely exemplary and not exhaustive.

Additionally, the introduction of novel contact lens packaging that deviates from the traditional blister package often presents a challenge to wearers. Novel form factors and modalities may not be immediately intuitive. This frequently leads to frustration and/or lens becoming damaged or desterilized during the opening process. It would therefore be advantageous to provide a contact lens package with visual or tactile cues that make novel contact lens packages and opening experiences more intuitive.

Thus, there remains a need for contact lens packages which provide a consistent single touch or zero touch lens removal experience, effective solution management, or addresses one or a combination of the aforementioned challenges or deficiencies.

II. SUMMARY

It has now been found that some or all the foregoing and related objects may be attained in a contact lens package having one or more aspects described herein.

Various examples include a device for storage and application of a contact lens. In some examples, the device includes an applicator cap including a handle portion having a first end, a second end, and a body that extends between the first end and the second end. The body includes at least one lever surface. The device includes a container having a reservoir configured to house a contact lens and packaging solution. The at least one lever surface is configured to provide at least one leverage point for movement of the applicator cap relative to the container. The second end is configured to form a seal against a convex surface of the contact lens.

In some examples, the device includes comprising a seal wrap disposed about the applicator cap and the container, wherein the seal wrap is configured to secure the applicator cap and the container together.

In some examples, the container includes at least one seal surface. The at least one seal surface of the container abuts the applicator cap when the device is in a closed configuration.

In some examples, the at least one seal surface of the container includes an angular platform.

In some examples, the at least one seal surface of the container further include threads configured to engage with corresponding grooves of the applicator cap.

In some examples, the at least one seal surface of the container includes a plurality of concentric circular seals.

In some examples, the container includes polypropylene.

In some examples, the applicator cap includes a convex surface opposite and spaced apart from the handle.

In some examples, the applicator cap further includes a plurality of fins that define a plurality of reservoir channels in the convex surface of the applicator cap. The reservoir channels are configured to retain packaging solution.

In some examples, the applicator cap includes at least one seal surface. The at least one seal surface of the applicator cap abuts the container when the device is in a closed configuration.

In some examples, the at least one seal surface of the applicator cap includes a plurality of concentric circular seals.

In some examples, the at least one seal surface of the applicator cap includes threads configured to engage with corresponding grooves of the container.

In some examples, the at least one seal surface of the applicator cap is configured to fluidically seal against the container.

In some examples, the applicator cap includes polypropylene.

In some examples, the applicator cap and the container are made of a uniform material.

In some examples, the at least one lever surface is configured to rotate the applicator cap about an edge of the container.

In some examples, the handle portion includes a curved first surface, and a curved second surface opposite and spaced apart from the first curved surface, one of the first and second curved surfaces defining a finger receiver.

In some examples, the applicator cap includes a dimple extending away from the handle portion.

In some examples, the at least one lever surface is a rotational lever configured to rotate the applicator cap about a central axis of the container in a first direction.

In some examples, the handle portion includes a helical first surface and a helical second surface opposite and spaced apart from the helical first surface.

In some examples, the container includes a handle portion having a first end, a second end, and a body that extends between the first end and the second end. The body includes at least one lever surface. The at least one lever surface is a rotational lever configured to rotate the container about a central axis of the applicator cap in a second direction opposite of the first direction.

In some examples, the handle portion of the container includes a helical first surface and a helical second surface opposite and spaced apart from the helical first surface.

In some examples, the handle portion of the applicator cap, and the handle portion of the container, are each configured to provide rotational forces opposite each other.

In some examples, the container comprises a concave surface that defines the reservoir.

Various examples also include a method of applying a contact lens to a wearer's eye the contact lens stored in a package comprising an applicator cap including a handle portion having a first end, a second end, and a body that extends between the first end and the second end, wherein the body includes at least one lever surface; and a container having a reservoir configured to house a contact lens and packaging solution, wherein the at least one lever surface is configured to provide at least one leverage point for movement of the applicator cap relative to the container, and wherein the second end is configured to form a seal against a convex surface of the contact lens. The method includes rotating the handle portion with the leverage point, breaking the seal between the convex surface of the contact lens and the second end of the applicator cap, removing a contact lens from the convex surface, and applying the contact lens to the wearer's eye.

In some examples, rotating the handle portion includes rotating the handle portion about an edge of the container.

In some examples, rotating the handle portion includes rotating the handle portion about a central axis of the container.

Various examples also include a method of packaging a contact lens. The method includes providing packaging solution in a container, providing a cap with a convex surface that is sealable with the container, providing a contact lens in a convex up orientation in the convex surface forming a seal, and sealing the container by pressing the lid to the container.

III. BRIEF DESCRIPTION OF THE DRAWINGS

The foregoing and other features and advantages of the invention will be apparent from the following, more particular description of preferred embodiments of the invention, as illustrated in the accompanying drawings.

Figure 1:
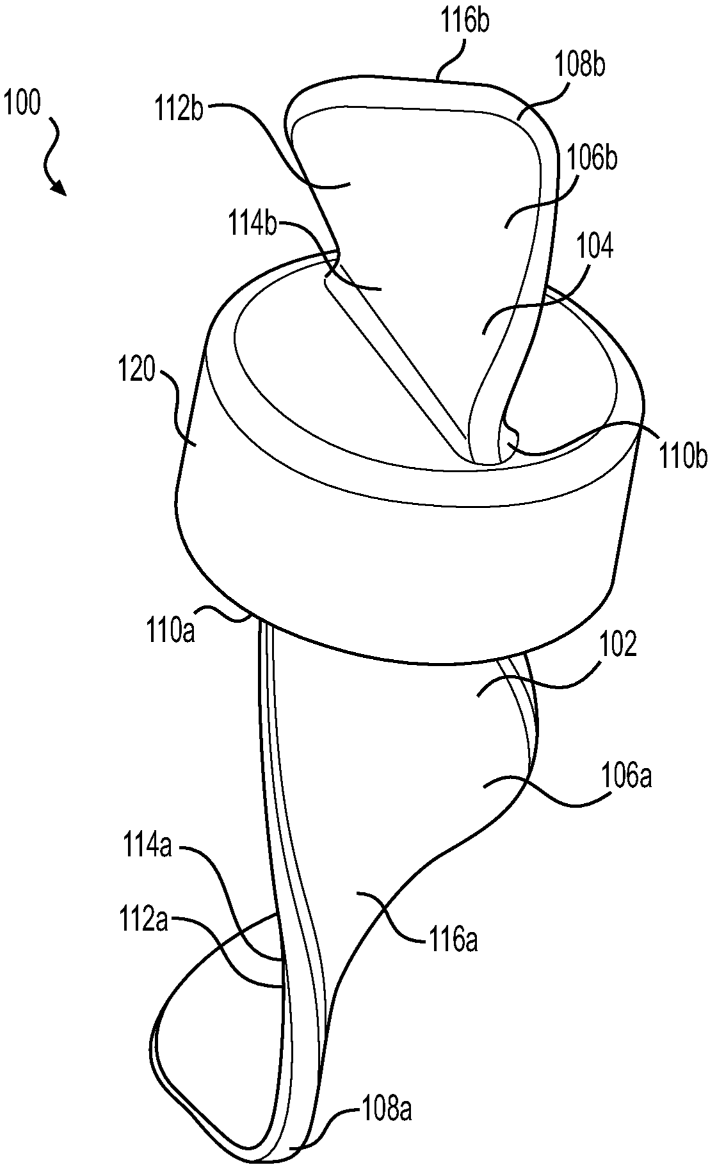
FIG. 1 illustrates a perspective view of a contact lens package in a closed configuration according to one example.
Figure 5A:
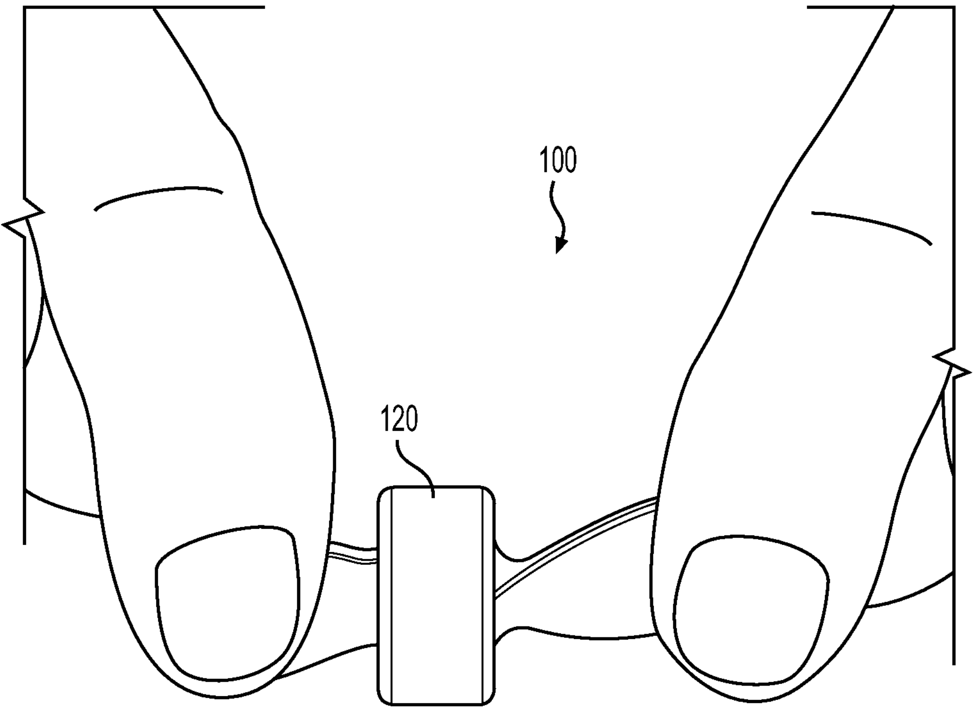
Figure 5B:
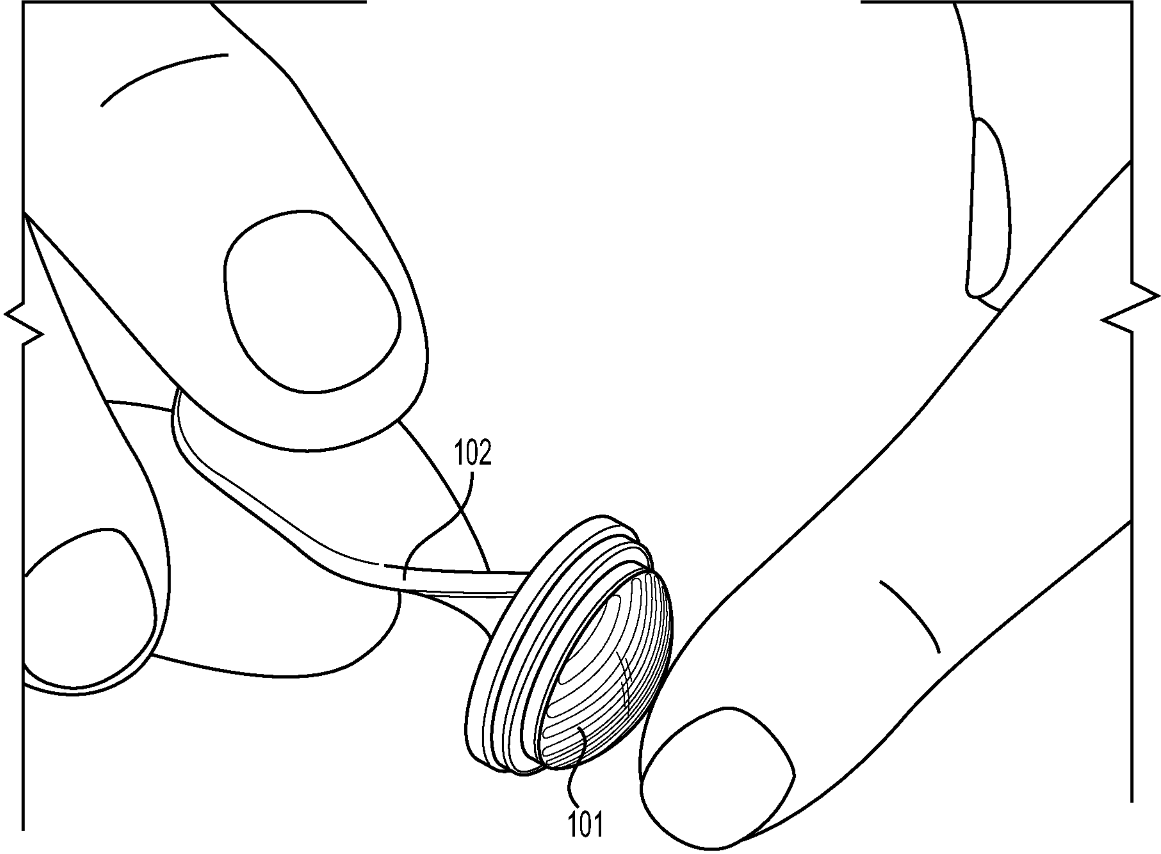
Figure 5C:
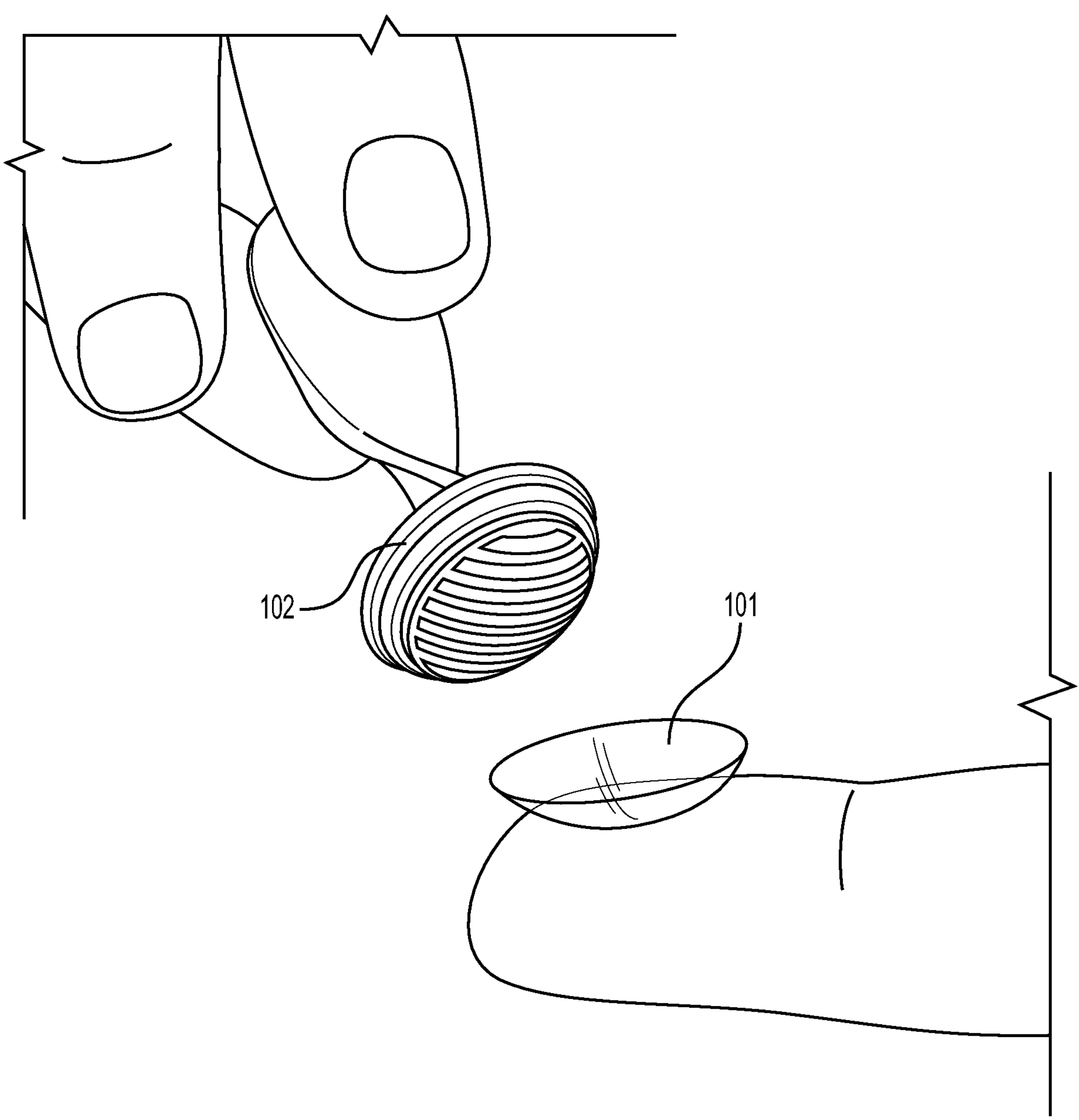

FIGS. 5A-C illustrate the contact lens package of FIG. 1 and steps of opening the contact lens package, to remove a contact lens according to one example. FIG. 5A illustrates how the cap and the container are twisted to open the container. FIG. 5B illustrates how the contact lens is disposed on the cap once the package is opened. FIG. 5C illustrates how a user removes the contact lens from the cap.

Figure 6:
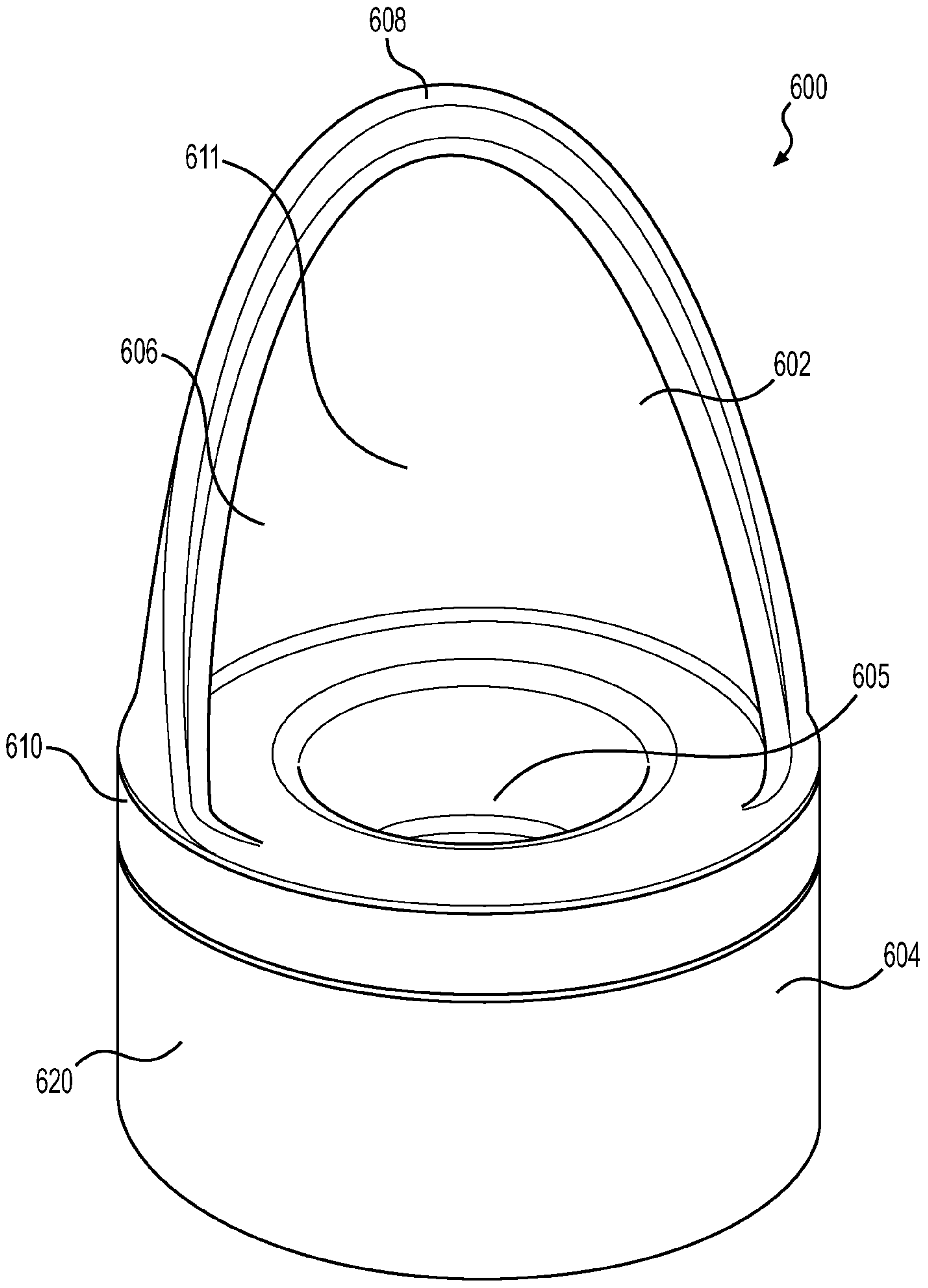

FIG. 6 illustrates a perspective view of a contact lens package in a closed configuration according to another example.

Figure 7:
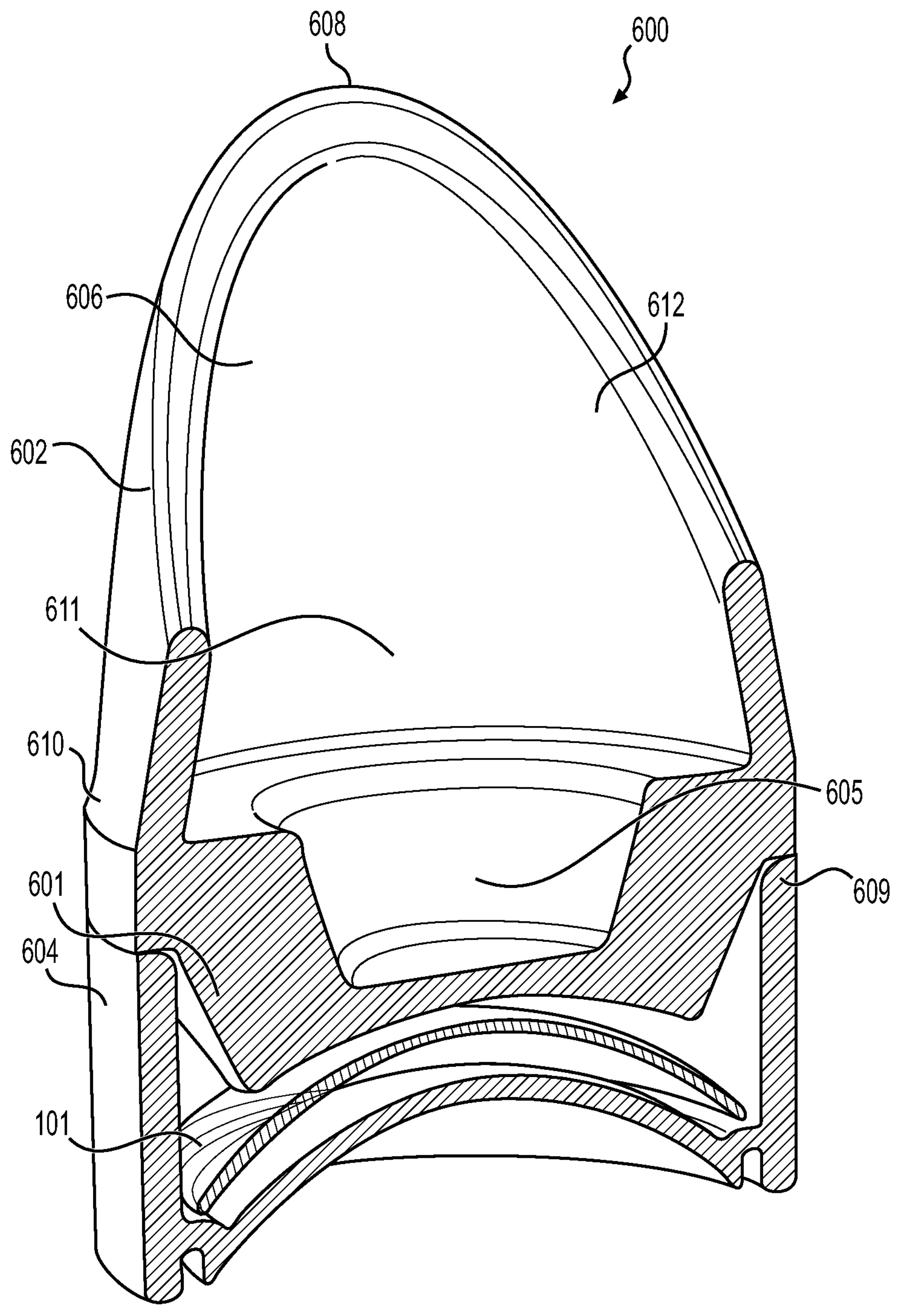

FIG. 7 illustrates a cutaway perspective view of the contact lens package shown in FIG. 6 in a closed configuration.

Figure 8:
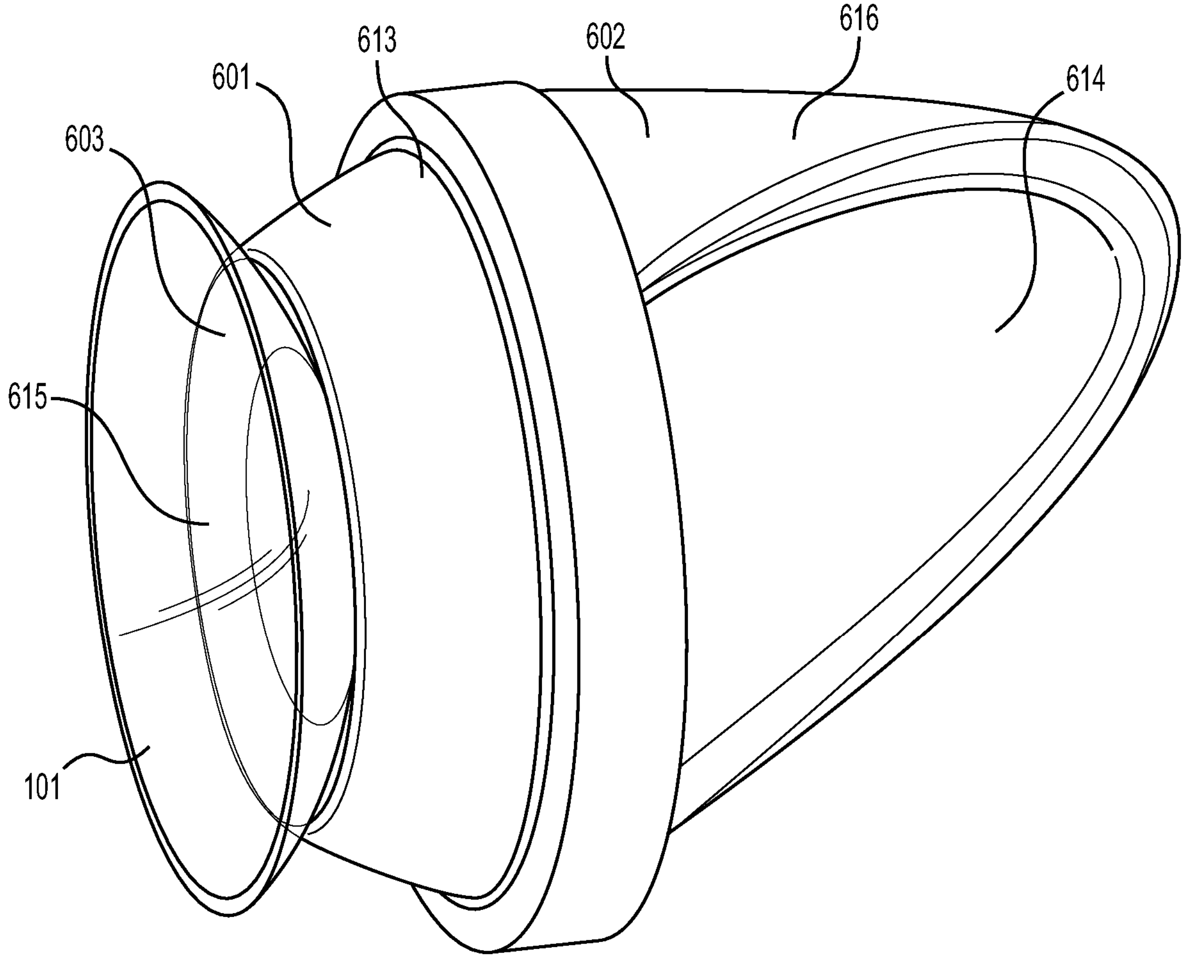

FIG. 8 illustrates a perspective view of a cap of the contact lens package shown in FIG. 6.

Figure 9:
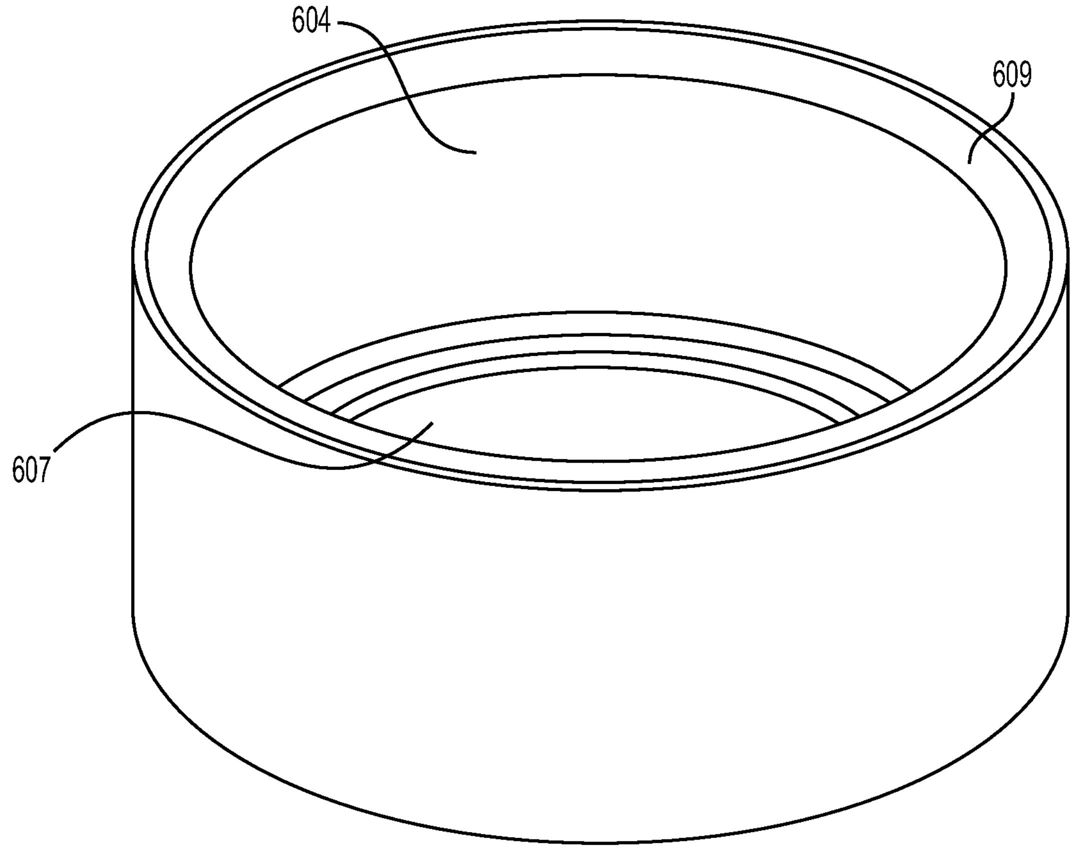

FIG. 9 illustrates a perspective view of a container of the contact lens package shown in FIG. 6.

Figure 10A:
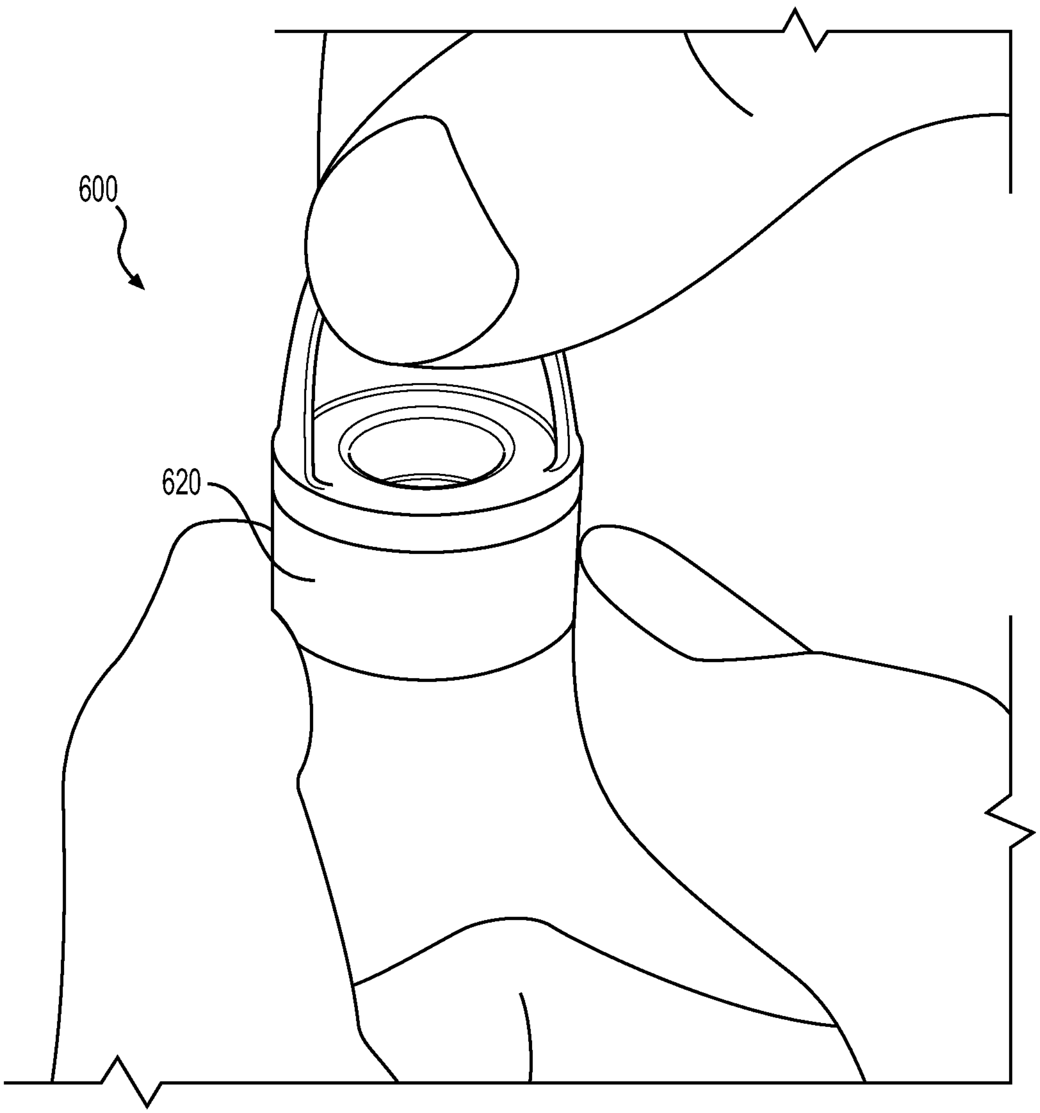
Figure 10B:
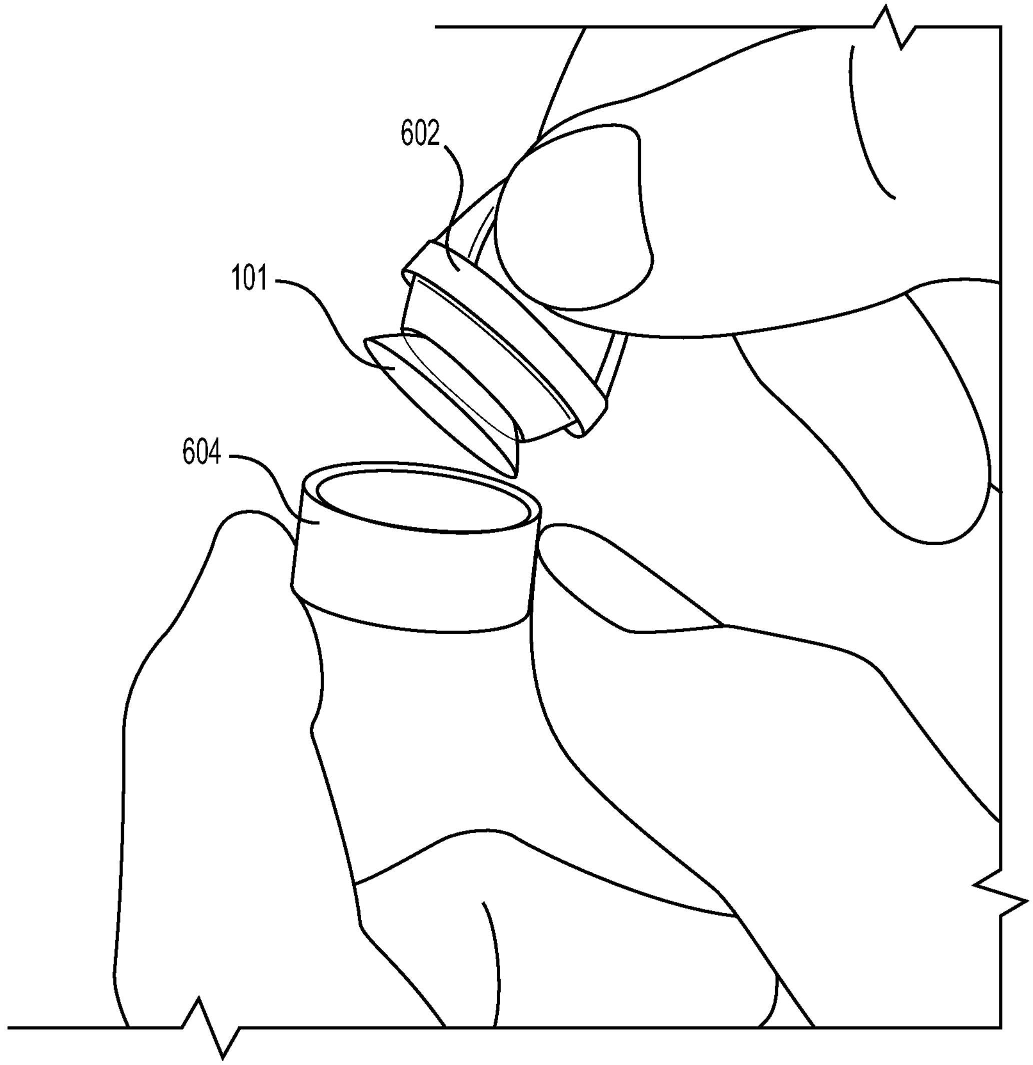
Figure 10C:
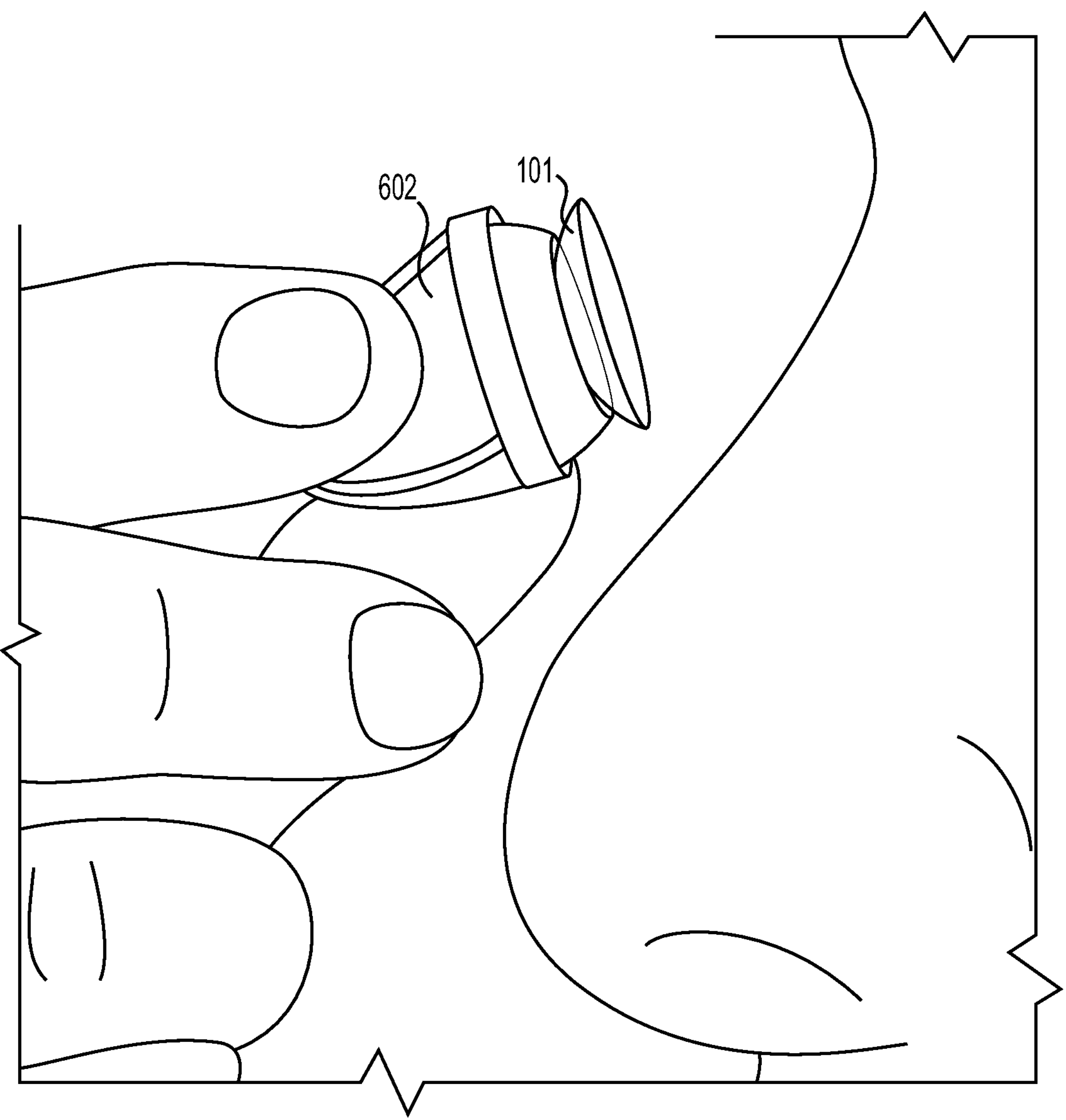

FIGS. 10A-C illustrate the contact lens package of FIG. 6 and steps of opening the contact lens package, to remove a contact lens according to one example. FIG. 10A illustrates how the cap is rotated to open the container. FIG. 10B illustrates how the cap is separated from the container. FIG. 10C illustrates how a user applies the contact lens using the cap.

IV. DETAILED DESCRIPTION

Reference will now be made in detail to representative embodiments illustrated in the accompanying drawings wherein reference numerals indicate certain elements. The following descriptions are not intended to limit the myriad embodiments to one preferred embodiment. To the contrary, it is intended to cover alternatives, modifications, and equivalents as can be included within the spirit and scope of the described embodiments as defined by the appended claims.

References to "one embodiment," "an embodiment," "some embodiments," "an example embodiment," etc., indicate that the embodiment described may include a particular feature, structure, aspect, or characteristic, but every embodiment may not necessarily include the particular feature, structure, or characteristic. Moreover, such phrases are not necessarily referring to the same embodiment. Further, when a particular feature, structure, aspect, or characteristic is described in connection with an embodiment, it is submitted that it is within the knowledge of one skilled in the art to effect such feature, structure, or characteristic in connection with other embodiments whether or not explicitly described.

Lens(es) or contact lens(es) refer to ophthalmic devices that reside on the eye. They have a generally hemispheric shape and can provide optical correction, cosmetic enhancement, UV blocking and visible light or glare reduction, therapeutic effect, including wound healing, delivery of drugs or neutraceuticals, diagnostic evaluation or monitoring, or any combination thereof. The term lens includes soft hydrogel contact lenses, which are generally provided to the consumer in a package in the hydrated state, and have a relatively low moduli, which allows them to conform to the cornea. Contact lenses suitable for use with the packages of the present invention include all hydrated contact lenses, including conventional and silicone hydrogel contact lenses.

A hydrogel is a hydrated crosslinked polymeric system that contains water in an equilibrium state, and may contain at least about 25%, or at least 35% water in the hydrated state. Hydrogels typically are oxygen permeable and biocompatible, making them excellent materials for producing contact lenses.

Conventional hydrogel contact lenses do not contain silicone containing components, and generally have higher water content, lower oxygen permeability, moduli, and shape memories than silicone hydrogels. Conventional hydrogels are prepared from monomeric mixtures predominantly containing hydrophilic monomers, such as 2-hydroxyethyl methacrylate ("HEMA"), N-vinyl pyrrolidone ("NVP") or polyvinyl alcohols. U.S. Pat. Nos. 4,495,313, 4,889,664 and 5,039,459 disclose the formation of conventional hydrogels. Conventional hydrogels may be ionic or non-ionic and include polymacon, etafilcon, nelfilcon, ocufilcon lenefilcon and the like. The oxygen permeability of these conventional hydrogel materials is typically below 20-30 barrers.

Silicon hydrogel formulations include balafilcon samfilcon, lotrafilcon A and B, delfilcon, galyfilcon, senofilcon A, B and C, narafilcon, comfilcon, formofilcon, riofilcon, fanfilcon, stenfilcon, somofilcon, kalifilcon and the like. "Silicone hydrogels" refer to polymeric networks made from at least one hydrophilic component and at least one silicone-containing component. Silicone hydrogels may have moduli in the range of 60-200, 60-150 or 80-130 psi, water contents in the range of 20 to 60%. Examples of silicone hydrogels include acquafilcon, asmofilcon, balafilcon, comfilcon, delefilcon, enfilcon, fanfilcon, formofilcon, galyfilcon, lotrafilcon, narafilcon, riofilcon, samfilcon, senofilcon, somofilcon, and stenfilcon, verofilcon, including all of their variants, as well as silicone hydrogels as prepared in U.S. Pat. Nos. 4,659,782, 4,659,783, 5,244,981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9,156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties. Silicone hydrogels may have higher shape memory than conventional contact lenses.

Hydrogel lenses are viscoelastic materials. Contact lenses can form optical distortions if the lens interacts with either the package or any air bubble in the package. The extent of the optical distortions, and the length of time needed for the distortions to relax out will vary depending on the chemistry, and to a lesser extent, geometry of the lens. Conventional lens materials, such as polyhydroxyethyl methacrylate-based lenses like etafilcon A or polymacon have low loss modulus and tan delta compared to silicone hydrogels and may form fewer and less severe optical distortions as a result of contact with packaging. The incorporation of silicones (which generally increase the bulk elastic response), wetting agents such as PVP (which generally increase the viscous response) or coatings of conventional hydrogel materials (which may lower the elastic response at the lens interface) can alter the lens viscoelastic properties. Conventional hydrogel contact lenses and silicone hydrogel contact lenses having short or stiff crosslinking agents and or stiffening agent have short shape memories and may be less susceptible to deformation during storage. As used herein, high or higher shape memory hydrogels display optical distortions from contact with an air bubble or package of at least about 0.18 after 5 weeks of accelerated aging at 55° C. Viscoelastic properties, including loss modulus and tan delta, can be measured using a dynamic mechanical analysis.

The contact lenses can be of any geometry or power, and have a generally hemispherical shape, with a concave posterior side which rests against the eye when in use and a convex anterior side which faces away from the eye and is contacted by the eyelid during blinking.

The center or apex of the lens is the center of the lens optic zone. The optic zone provides optical correction and may have a diameter between about 7 mm and about 10 mm. The lens periphery or lens edge is the edge where the anterior and posterior sides meet.

The wetted lens is the contact lens and any residual packaging solution attached to it after packaging solution drainage. Wetted contact is the aggregated contact area between the wetted lens and lens support.

Embodiments may include a lens support (e.g., a platform as described herein) surrounded by a sealable cavity also interchangeably referred to as a chamber. The cavity may have any convenient form and may comprise a package base (also interchangeably referred to as a container) and at least a lid, each of which are described in detail below. As used herein, the phrases "the lid", "a lid", "the base" and "a base" encompass both the singular and plural. The lid and package base are sealed to each other to form a cavity which holds the contact lens, support and packaging solution in a sterile state during shipping and storage prior to use. The contact lens package is made from materials which are compatible with the contact lens and solution, as well as retortable and biologically inert.

"Film" or "multilayer film" are films used to seal the package and are often referred to as lidstock. Multilayer films used in conventional contact lens packages may be used in the packages of the present invention as the base, a component of the lid, or both. Multilayer films comprise a plurality of layers, including barrier layers, including foil layers, or coatings, seal layers, which seal the film to the rest of the package, and may also comprise additional layers selected from peel initiation layers, lamination layers, and layers that improve other package properties like stiffness, temperature resistance, printability, puncture resistance, barrier resistance to water or oxygen and the like. The multilayer films form a steam sterilizable (retortable) seal. The multilayer film can include PET, BON or OPP films layers to increase stiffness and temperature resistance, or to EVOH or PVDC coatings to improve barrier resistance to oxygen or moisture vapor.

An "unopened state" or "unopened" as used herein refers to a contact lens package that is closed and houses a contact lens in solution.

An "opened state" or "opened" as used herein refers to a contact lens package after the sterile seal has been broken. Depending on the context described herein, the open state extends to the state of the package when the user has manipulated the package to cause the lens to be lifted out of the packaging solution for transfer by the user.

A "wearer" or "user" as used herein refers to a person opening a contact lens package. The user is generally referred to as the person who both opens the package and transfers the contact lens contained therein to their eye. However, the user in some contexts may be a person handling the lens package on behalf of the wearer, such an eye care provider ("ECP") or another individual demonstrating for or assisting the wearer.

Packaging solution is any physiologically compatible solution, which is compatible with the selected lens material and packaging. Packaging solutions include buffered solutions having a physiological pH, such as buffered saline solutions. The packaging solution may contain known components, including buffers, pH and tonicity adjusting agents, lubricants, wetting agents, nutraceuticals, pharmaceuticals, in package coating components and the like.

The package base may form the bottom of the package. It can be made from any material suitable for packaging medical devices, including plastic. Suitable materials include polyolefins including polypropylene, and olefin co-polymers, including COPs (Cyclic Olefin Polymer) and COCs, (Cyclic Olefin Co-polymers), and blends thereof. The packaging lid generally resides at the upper portion the package and seals with the base to form a cavity containing at least a portion of the lens support, lens, and packaging solution. The lid may be made from any material suitable for packaging medical devices, including a molded sheet of foil or plastic, laminate films, or plastic. Packages comprising plastic for one structure and foil or laminated films as the other, or packages comprising foil or laminated films as the outer layer for the lid and base are known in the art and are examples of suitable combinations.

References throughout this description to injection molding processes and the use of materials conventionally applied to injection molding should be understood as exemplary. Those of skill in the art will appreciate that other means of manufacture are possible within the scope of the appended claims, including but not limited to alternative molding processes, thermoforming, 3D printing, and the like. Likewise, references to heat seals and heat sealing are exemplary to embodiments described herein. Other means of securing packaging components will be apparent to those skilled in the art, including the use of adhesive, glue, thermal bonding, welding such as heat, ultrasonic or laser welding, or a mechanical trap, and the like.

Certain aspects of the invention may serve to reduce or prevent significant optical damage to the contact lens due to interactions with air bubbles or the interior of the lens package that may arise during storage or transit due to gravitational or other forces, such as mechanical pressure being applied from outside of the package. As used herein, significant optical damage means a root-mean-squared (RMS) value equal or greater than about 0.08 μm.

With reference to the figures, FIG. 1 illustrates a contact lens package 100. The package 100 is formed to provide a single-touch application by a user, such that a contact lens 101 stored in the package 100 can be removed from the package 100 and applied with only one instance of contact with a user. Further, the package 100 provides levers to easily twist the package 100 open. FIG. 1 shows a contact lens package 100 that includes an applicator cap 102, and a container 104 that is pivotably coupled to the cap 102. The applicator cap 102 and the container 104 are sealedly coupled together to provide a sterile internal environment between the applicator cap 102 and the container 104.

The applicator cap 102 is a substantially rigid cap 102 that provides a sterile enclosure when coupled to the container 104. The cap 102 also provides a handle (in this particular embodiment a helical shaped handle) configured to allow for twisting and rotating the cap 102 at least about a central axis 111 of the container such that a user can open the package 100 at least in part by twisting the cap 102. The handle also provides an interface for a user to manipulate the lens 101 without touching it. The cap 102 also provides a contact surface against the concave surface of a contact lens 101, such that the contact lens 101 is retained on the cap 102 at least in part by a surface tension. As described in more detail below, the cap 102 includes a plurality of fins 103 and a plurality of reservoir channels 105. The fins 103 are configured to contact the concave surface of the lens 101, and the channels 105 are configured to retain solution. This disclosure contemplates that the size and/or shape of the fins 103 can be selected to provide a desirable amount of surface tension in order to retain the lens 101. The surface tension force between finger and lens is roughly equal to (or slightly less than) the weight of the lens. If the lens is dabbed off the support upside down, as illustrated herein (e.g., in FIG. 5B), the wetted contact area that the lens can tolerate is to roughly double compared to a lens support that is used with the lens the 'right way' up due to the pull of gravity. In either case, to permit single-touch transfer, the fins should be configured such that the surface tension produced by the wetted contact area between the lens support and the lens is less than that the surface tension produced created between the finger and the lens upon dabbing. Additionally, the channels 105 reduce the surface tension, which makes the transitioning the lens 101 from the cap 102 to the user's finger easier. Channels 105 preferably are made wide enough not to traps solution behind the lend 102, i.e., at least about 1 mm in width and likewise should be sufficiently tall that they are self-draining and thus draw fluid away from the lens 101 during opening. Preferably the channels are at least 2 mm tall beneath the apex of the lens. The cap 102 includes a handle portion 106*a* having a first end 108*a*, a second end 110*a*, and a body 112*a* that extends between the first end 108*a* and the second end 110*a*. The body 112*a* includes a first lever surface 114*a* and a second lever 116*a* surface opposite and spaced apart from the first lever surface 114*a*. Each lever surface 114*a*, 116*a* is configured to provide at least one leverage point for movement of the applicator cap 102 relative to the container 104.

Figure 2:
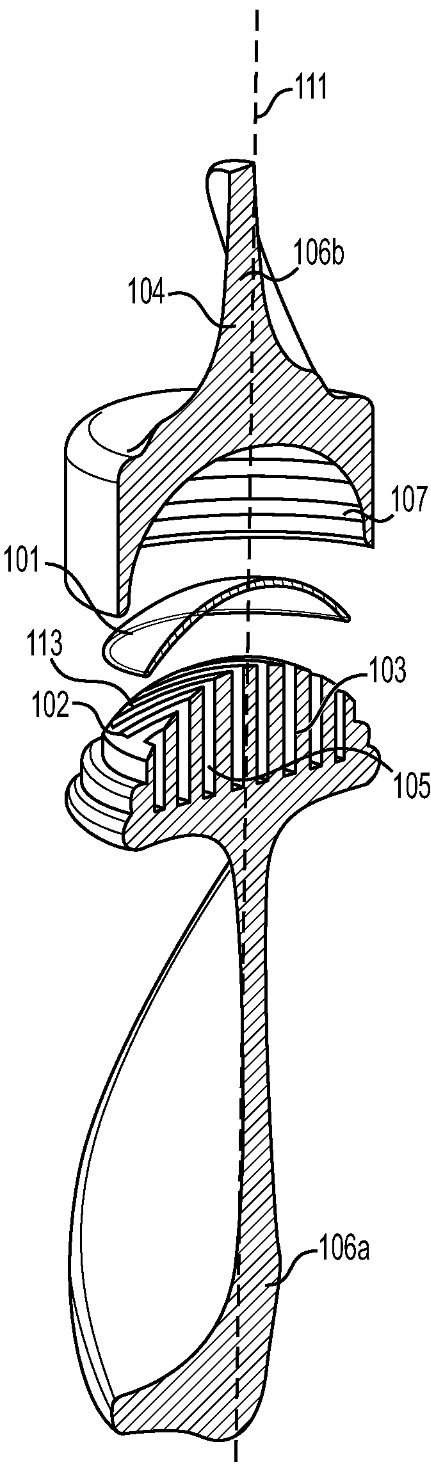
FIG. 2 illustrates a cutaway exploded perspective view of the contact lens package shown in FIG. 1 in a closed configuration.

In the example shown in FIG. 2, the cap 102 also includes a spherical dome having a convex surface 113 arranged at the second end 110 of the handle portion. The convex surface 113 provides a dome-like surface that is formed to abut a concave surface of a contact lens 101. Surface tension between the dome-like surface provided by the convex surface 113 and the concave surface of the lens 101 holds the lens 101 in place. In some embodiments, the convex surface 113 includes a dimple (not shown) in the center of the dome to provide a recess for a finger to mold into when dabbing. The cap 102 also includes fins 103 that define reservoir channels 105 in the convex surface 113 of the cap 102. In FIG. 2, the fins 103 and channels 105 are equally sized and spaced from one another. It should be understood that this arrangement is provided only as an example. This disclosure contemplates that the number, size, and/or shape of the fins 103 and channels 105 may be different than shown in FIG. 2. In particular, the number, size, and/or shape of the fins 103 and channels 105 may be selected to provide a desirable amount of surface tension between the lens 101 and the cap 102 to facilitate moving the lens 101 from the cap 102 to a user's finger. The reservoir channels 105 are provided to retain packaging solution. Each of the fins 103 extend away from the handle portion 106 and include fin surfaces that form the dome-like surface described above. The fins 103 are angled away from the center of the convex surface 113 and extend at decreasing lengths toward the edges of the convex surface. For example, fins 103 extending at edges of the convex surface 113 are shorter than fins 103 extending from the center of the convex surface 113.

Figure 3:
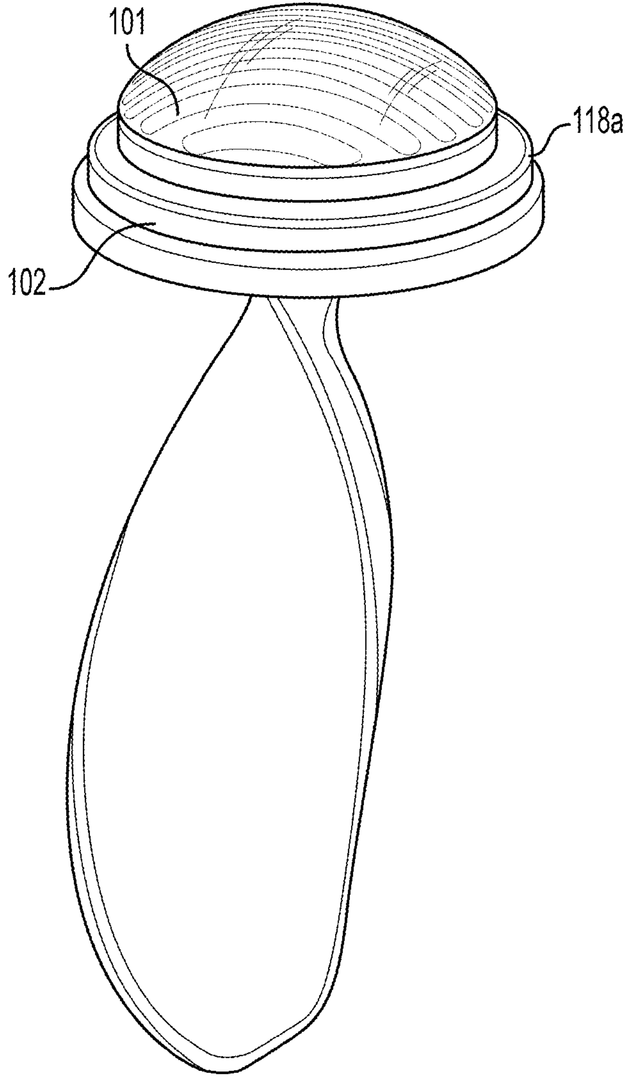
FIG. 3 illustrates a perspective view of a cap of the contact lens package shown in FIG. 1.

In the example shown in FIG. 3, the cap 102 also includes a plurality of seal surfaces 118*a*. The seal surfaces 118*a* correspond to seal surfaces 118*b* of the container 104 (described below). The seal surfaces 118*a* are provided to abut the container 104 forming a sterile seal when the package 100 is in a closed configuration. In the example shown in FIG. 3, the seal surfaces 118*a* are five concentric circular tiered surfaces extending further away from the handle portion 106 toward the center of the cap 102. Although in other examples, the seal surfaces 118 can be any other shape or number suitable to form sterile seals against the container 104. In some examples, the seal surfaces 118*a* are threads configured to interact with corresponding grooves on the container 104, creating a fluidic seal. In some examples such as the example shown in FIG. 1, a seal wrap 120 formed from aluminum foil is disposed about a circumference of the cap 102 and the container 104 forming a mechanical and fluidic seal between the cap 102 and the container 104. The wrap 120 is anisotropic such that it is weaker in shear strength than either of its longer dimensions, which results in the wrap 120 tearing responsive to twisting the cap 102 relative to the container 104. In the example shown in FIG. 1, the cap 102 is made of polypropylene. But, in other examples the cap can be made from any other material suitable to enclose a contact lens 101 in a sterile environment. In the example shown in FIG. 1, the seal 120 disposed about a circumference of the cap 102 is aluminum foil. But in other examples, the seal disposed about the circumference of the cap is waxed paper, polyester sheet, or any other material suitable to seal a cap and a container together forming a sterile environment.

Figure 4:
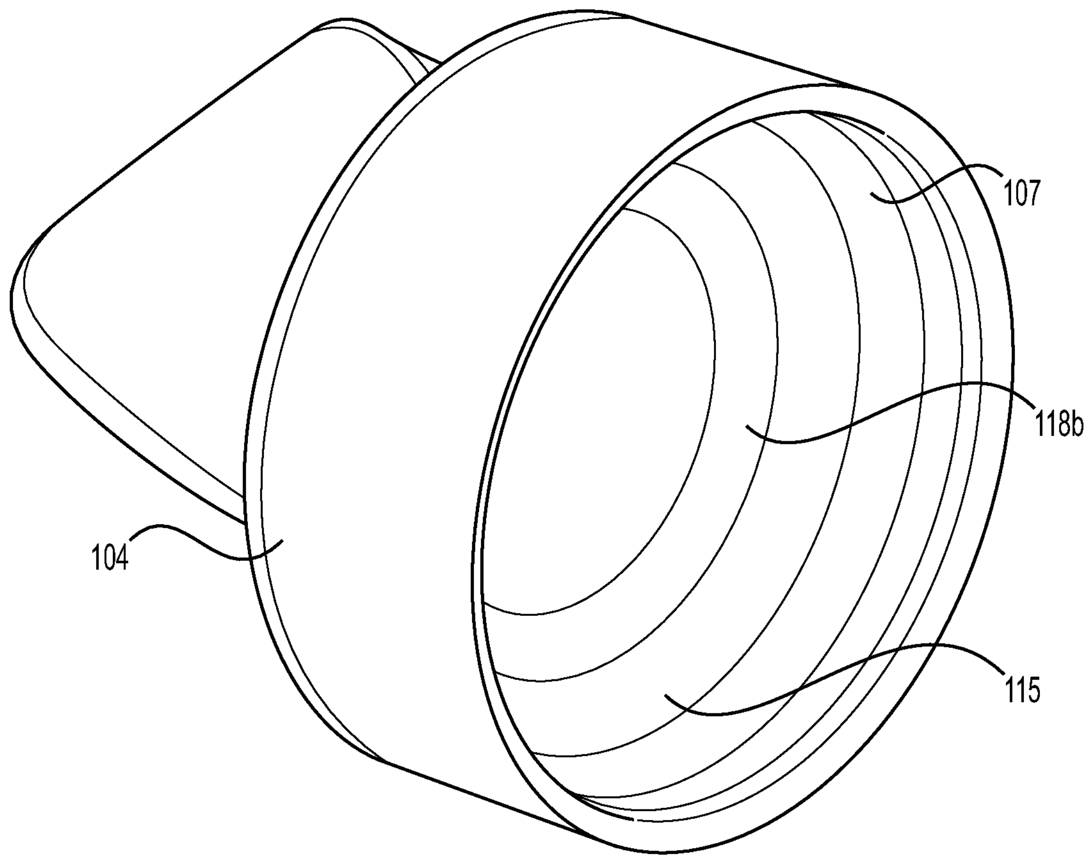
FIG. 4 illustrates a perspective view of a container of the contact lens package shown in FIG. 1.

The container 104 is a substantially rigid container 104 provided to enclose and retain a contact lens 101 and packaging solution in a sterile environment when coupled to the cap 102. The container 104 also provides a helical-shaped manipulatable handle for twisting and rotating the container 104 such that a user can open the package 100 at least in part by twisting the container 104. As shown in FIG. 4, the container 104 includes a reservoir 115 that can house a contact lens 101 and packaging solution. The container 104 includes a handle portion **106*b* and a cylindrical portion with a concave dome shaped inner surface 107 that extends away from the handle portion 106*b*. Preferably, inner surface 107 includes recessed areas (e.g. ribs or channels (not shown)) to reduce the surface area between inner surface 107 and the lens 101 so that the lens preferentially sticks to the convex surface 113. If the difference in surface area is large enough, then the pack can be opened in any orientation. Similar to the handle portion 106*a* of the cap 102, handle portion 106*b* of the container 104 has a first end 108*b*, a second end 110*b*, and a body 112*b* that extends between the first end 108*b* and the second end 110*b*. The body 112*b* includes a first lever surface 114*b* and a second lever surface 116*b* opposite and spaced apart from the first lever surface 114*b*. Each lever surface 114*b*, 116*b* is configured to provide at least one leverage point for movement of the container 104 relative to the applicator cap 102**.

In the example shown in FIG. 4, the container 104 also includes a plurality of seal surfaces **118*b* surrounding the dome shaped inner surface 107. The seal surfaces 118*b* are provided to abut the cap 102 forming a sterile seal when the package 100 is in a closed configuration. In the example shown in FIG. 4, the seal surfaces 118*b* are five concentric circular tiered surfaces axially spaced apart along the dome shaped inner surface 107. Although, in other examples, the seal surfaces can be any other shape or number suitable to form sterile seals against the container 104. In some examples, the seal surfaces are threads configured to interact with corresponding grooves on the container 104, creating a fluidic seal. In the example shown in FIG. 1, the container 104 is made of polypropylene. In some examples, the cap 102 and the container 104 each include tiered surfaces that abut each other. In some other examples, the cap 102 and the container 104 each include threads that interlock with each other. In some examples the cap 102 and the container 104 are made of a uniform material, but in other examples, the cap 102 and the container 104** are each formed from a separate material.

In the example shown in FIGS. 1-4 the handle portions **106*a* and 106*b* of the cap 102 and container 104 are helical. But in other examples, the handle portions 106*a* and 106*b* are, otherwise curved or shaped to provide a lever for rotation of the cap 102 and the container 104 relative to each other. In the example shown in FIGS. 1-4 the cap 102 and the container 104 each have a handle portion 106*a* and 106*b*, but in other examples, only one of the cap 102 or the container 104 include a handle portion. In the example shown in FIGS. 1-4 the handle portion 106*a* of the cap 102 and the handle portion 106*b* of the container 104 are each the same shape, but in other examples, the handle portion 106*a* of the cap 102 is a different shape than the handle portion 106*b* of the container 104. The cap 102 and the container 104 are each formed from a uniform material-polypropylene, for example. But in other examples, the cap 102 and the container 104 are formed from any other material suitable to support a contact lens 101 in a sterile environment. In some further examples, the cap 102 and the container 104 are formed from different materials such that the cap 102 is formed from a first material, and the container 104 is formed from a second material. The components described herein can be formed by injection molding, extrusion, 3D printing, or any other manufacturing method suitable for forming a sterile contact lens package 100**.

FIG. 5A shows a user opening the package 100 described above and shown in FIGS. 1-4. FIG. 5A shows the user twisting a container 104 relative to cap 102 to open the package 100 by grasping the first lever surface **114*a* and the second lever surface 116*a* of the cap 102 and grasping the first lever surface 114*b* and the second lever surface 116*b* of the container 104. For example, the user grasps one of the first lever surface 114*a* of the cap 102 and the first lever surface 114*b* of the container 104 with an index finger, and the user grasps one of the second surface lever surface 116*a* of the cap 102 and the second surface lever surface 116*b* of the container 104 with a thumb. The user twists the handle portion 106*a* of the cap 102 and the handle portion 106*b* of the container 104 to break the seal between the cap 102 and the container 104. FIG. 5B shows a contact lens 101 attached to the cap 102 by surface tension between the convex surface of the cap 102 and the concave surface of the lens 101. The lens 101 is presented on the surface that allows it to be transferred to the user's finger with a single touch. FIG. 5C shows the user removing the cap 102 using one finger to remove the contact lens 101 from the cap 102 using a single touch. The lens 101 is precisely positioned on the user's finger in the correct orientation for insertion into the eye. The user has one point of contact with the lens 101, as the lens 101** can remain in the same orientation with respect to the user's finger and is placed on the user's eye.

The lens concave portion shown in the present examples preferably allow, upon dabbing, both the fingertip and lens to deform to match each other's shape, without causing lens inversion or damage to lens during removal from too much pressure during dabbing. Thus, an aspect of the removal of the lens from the present packages is to control the ratio of the contact area between the finger and lens as compared to the area between the lens and the lens support so that the contact area between the finger and lens exceeds the contact surface area of the lens support on the lens underside. This will ensure that surface tension between finger and lens exceeds surface tension between lens and lens support. Thus, the lens will adhere to the finger for lens transfer and placement onto the eye.

With reference to the figures, FIG. 6-8 illustrate a contact lens package 600. The package 600 is formed to provide a no-touch application by a user. As such, a user can apply a contact lens 101 directly to an eye by manipulating the package 600. FIG. 6 shows a contact lens package 600 that includes an applicator cap 602, and a container 604 that is pivotably coupled to the cap 602.

The applicator cap 602 is a substantially rigid cap 602 that provides a sterile enclosure when coupled to the container 604. The cap 602 also provides a manipulatable handle for twisting and rotating the container 604 such that a user can twist the container 604 at least in part by twisting the cap 602. The handle also provides an interface for a user to manipulate the lens without touching it as described above. The cap 602 further provides a sealed surface against the concave surface of a contact lens 101, such that the lens 101 is retained on the cap 602 at least in part by surface tension between cap 602 and the lens 101. The cap 602 includes a handle portion 606 having a first end 608, a second end 610, and a body 612 that extends between the first end 608 and the second end 610. The cap 602 also includes a concave circular surface 615 opposite and spaced apart from the handle portion 606 that is disposed on a lens platform 601. The handle portion 606 is an elongated body having a substantially curved cross section. For example, the body 612 of the handle portion 606 extends between the first end 608 and the second end 610. The body 612 of the handle portion 606 includes a curved first surface 614, and a curved second surface 616 opposite and spaced apart from the curved first surface 614 defining a finger receiver 611. The finger receiver 611 is an elongated curved opening extending along the handle portion 606 that at least partially wraps around a finger used to rotate the cap 602 with respect to the container 604. Each of the curved first surface 614 and curved second surface 616 are configured to provide at least one leverage point for movement of the applicator cap 602 relative to the container 604 and for manipulation of the cap 602 during application of a contact lens 101. The cap 602 also includes a dimple 605 extending away from the handle portion 606. The dimple 605 is a depression in the cap 602 that is provided to receive at least a portion of a user's fingertip, allowing the user to position a finger securely in the cap 602 for precise application of a contact lens 101 to an eye.

The lens platform 601 provides a contact surface with a convex surface of a contact lens 101. The lens platform 601 includes a concave surface 603 about a circular portion that extends from the second end 610 of the handle portion 606. The concave surface 603 forms a depression that can abut a convex surface of a contact lens 101 and secure the contact lens 101 in place. Surface tension between the concave surface 603 and the convex surface of the lens 101 hold the lens in place. The concave surface 103 is configured not to cover the entire convex surface of the lens 101 so that the lens can release onto the eye. Preferably, concave surface 103 covers less than about 50% of the convex surface area of the lens 101. The concave surface 603 provides a ring that is sized and shaped to retain surface tension between the concave surface 603 of the cap 602 and the convex surface of a contact lens 101. The platform 601 includes a tapered surface 613 that tapers away from the handle portion 606 providing an angled sealing surface to seal against the container 604.

In some examples, the cap also includes a plurality of seal surfaces. The seal surfaces are provided to abut the container forming a sterile seal when the package is in a closed configuration. The seal surfaces can be any other shape to form a sterile seal against the container. In some examples, the seal surfaces are threads configured to fluidically seal against the container.

The container 604 is a substantially rigid container 604 provided to enclose and retain a contact lens 101 and packaging solution in a sterile environment when coupled to the lid. The container 604 includes a reservoir that can house a contact lens 101 and packaging solution. The container 604 also includes a convex surface 607 at a base of the container 604 that is provided to abut the concave side of a contact lens 101, securing the lens 101 between the container 604 and the cap 602. The convex surface area preferably includes recessed regions (e.g., ribs or channels (not shown)) to reduce surface area and allow air to enter under the lens, so the lens preferentially sticks to the cap. The container 604 also includes a beveled inner surface 609 provided to abut the tapered portion of the platform 601 of the cap 602 forming a sterile seal.

In some examples, the container also includes a plurality of seal surfaces surrounding the dome shaped inner surface. The seal surfaces are provided to abut the cap forming a sterile seal when the package 600 is in a closed configuration. The seal surfaces can be any shape or number suitable to form sterile seals against the container 604. In some examples such as the example shown in FIG. 6, a seal wrap 620 formed from aluminum foil is provided and disposed about a circumference of the cap 602 and the container 604 forming a mechanical and fluidic seal against the cap 602 and the container 604. The wrap 620 is anisotropic such that it is weaker in torsion than either of its longer dimensions, which results in the wrap 620 tearing responsive to twisting the cap 602 relative to the container 604. In the example shown in FIG. 6, the container 604 is made of polypropylene. In some examples, the cap and the container each include tiered surfaces that abut each other. In some other examples, the cap and the container each include threads that interlock with each other. In some examples, the cap and the container are made of a uniform material, but in other examples, the cap and the container are each formed from a separate material.

In the example shown in FIGS. 6-9, the handle portion 606 of the cap 602 is curved and tapers away from the concave surface of the cap 602. But in other examples, the handle portion 606 is a uniform curved shape suitable to provide a lever for rotation of the cap 602 and the container 604 relative to each other. In the example shown in FIGS. 6-9, the cap 602 has a handle portion 606 and the container 604 does not have a handle portion 606. But, in other examples, both the cap 602 and the container 604 each include a handle portion 606, which can be the same shape as each other. In other examples, the handle portion 606 of the cap 602 is a different shape than the handle portion 606 of the container 604. The cap 602 and the container 604 are each formed from a uniform material—polypropylene, for example. But in other examples, the cap 602 and the container 604 are formed from any other material suitable to enclose a contact lens 101 in a sterile environment. In some further examples, the cap 602 and the container 604 are formed from different materials such that the cap 602 is formed from a first material, and the container 604 is formed from a second material. In the example shown in FIG. 6, the seal wrap 620 disposed about a circumference of the cap 602 is aluminum foil. But in other examples, the seal wrap 620 disposed about the circumference of the cap 602 is waxed paper, polyester sheet, or any other material suitable to seal a cap 602 and a container 604 together forming a sterile environment. The components described herein can be formed by injection molding, extrusion, 3D printing, or any other manufacturing method suitable for forming a sterile contact lens package 600.

FIG. 10A shows a user opening the package 600 described above and shown in FIGS. 6-9. FIG. 10A shows the user twisting a container 604 open by grasping the curved first surface 614 and the curved second surface of the cap 602 with one hand and grasping the container 604 with the other hand. The user grasps one of the curved first surface 614 or the curved second surface 616 of the cap 602 with an index finger, and the user grasps one of the curved first surface 614 or the curved second surface 616 of the cap 602 of the container 604 with a thumb. The user's thumb is in the elongated curved opening such that the user is touching the curved surfaces of the curved handle. The user twists the handle portion 606 of the cap 602 and the handle portion 606 of the container 604 to break the seal wrap 620 between the cap 602 and the container 604. FIG. 10B shows the user further pulling down on the handle portion 606 relative to the container 604 such that the cap 602 rotates about an edge of the container 604. FIG. 10B further shows a contact lens 101 still attached to the cap 602 by surface tension between the concave surface of the cap 602 and the convex surface of the lens 101 holding the lens 101 in place on the cap 602. FIG. 10C shows the user applying the lens 101 to their eye with the cap 602 (i.e., no touch). The lens 101 is applied to the user's eye using the curved handle such that the user never actually touches a surface of the contact lens 101. The lens 101 is applied directly from the cap 602 to the user's eye. The fluidic seal between the lens 101 and the cap 602 is broken once the lens 101 is adhered to a user's eye.

The lens concave portion shown in the present examples preferably allow application of a contact lens without causing lens inversion or damage to lens during removal from too much pressure during application. Thus, an aspect of the removal of the lens from the present packages is to provide an application surface that couples to a contact lens and can be separated from the contact lens without the user touching the lens. This will ensure that surface tension between eye and lens exceeds surface tension between lens and lens cap. Thus, the lens will adhere to the eye for lens transfer and placement onto the eye.

The visual and tactile cues as disclosed herein may be especially important for novel contact lens packages of the present invention, which departs significantly in form and method of opening from conventional contact lens packages. In a conventional package, the contact lens sits in a molded plastic base, having a bowl to receive the contact lens in a concave, bowl up position. Addition of visual or tactile features may create a more intuitive opening experience for the wearer.

The foregoing description, for purposes of explanation, used specific nomenclature to provide a thorough understanding of the described embodiments. However, it will be apparent to one skilled in the art that many of the specific details are not required in order to practice the described embodiments. Thus, the foregoing descriptions of the specific embodiments described herein are presented for the purposes of illustration and description. They are not targeted to be exhaustive or to limit the embodiments to the precise forms disclosed. It will be apparent to one of ordinary skill in the art that many modifications and variations are possible in view of the above teachings.

The Summary and Abstract sections may set forth one or more but not all exemplary embodiments of the present invention as contemplated by the inventors, and thus, are not intended to limit the present invention and the appended claims in any way.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The packages of the present invention may be manufactured using known materials and processes. The packaging materials may be virgin, recycled or a combination thereof. The volume within the package cavity can vary depending on the design selected.

Aspects of exemplary embodiments of the invention are further described with respect to the following clauses:

1. A device for storage and application of a contact lens, the device comprising:

an applicator cap comprising a handle portion having a first end, a second end, and a body that extends between the first end and the second end, wherein the body comprises at least one lever surface; and a container having a reservoir configured to house a contact lens and packaging solution, wherein the at least one lever surface is configured to provide at least one leverage point for movement of the applicator cap relative to the container.

2. The device of clauses 1, further comprising a seal wrap disposed about the applicator cap and the container, wherein the seal wrap is configured to secure the applicator cap and the container together.

3. The device of clauses 1 or 2, wherein the container comprises at least one seal surface, and wherein the at least one seal surface of the container abuts the applicator cap when the device is in a closed configuration.

4. The device of clauses 3, wherein the at least one seal surface of the container comprises an angular platform.

5. The device of clauses 3, wherein the at least one seal surface of the container further comprises threads configured to engage with corresponding grooves of the applicator cap.

6. The device of clauses 3, wherein the at least one seal surface of the container comprises a plurality of concentric circular seals.

7. The device of any one of the above clauses, wherein the container comprises polypropylene.

8. The device of any one of the above clauses, wherein the applicator cap comprises a convex surface opposite and spaced apart from the handle.

9. The device of clauses 8, wherein the applicator cap further comprises a plurality of fins that define a plurality of reservoir channels in the convex surface of the applicator cap, and wherein the reservoir channels are configured to retain packaging solution.

10. The device of any one of clauses 8 or 9, wherein the applicator cap comprises at least one seal surface, and wherein the at least one seal surface of the applicator cap abuts the container when the device is in a closed configuration.

11 The device of any one of clauses 8 or 9, wherein the at least one seal surface of the applicator cap comprises a plurality of concentric circular seals.

12. The device of any one of clauses 8 or 9, wherein the at least one seal surface of the applicator cap comprises threads configured to engage with corresponding grooves of the container.

13. The device of any one of clauses 8-12, wherein the at least one seal surface of the applicator cap is configured to fluidically seal against the container.

14. The device of any one of the above clauses, wherein the applicator cap comprises polypropylene.

15. The device of any one of the above clauses, wherein the applicator cap and the container are made of a uniform material.

16. The device of any one of the above clauses, wherein the at least one lever surface is configured to rotate the applicator cap about an edge of the container.

17. The device of any one of the above clauses, wherein the handle portion comprises a curved first surface, and a curved second surface opposite and spaced apart from the first curved surface, one of the first and second curved surfaces defining a finger receiver.

18. The device of any one of clauses 16 or 17, wherein the applicator cap further comprises a dimple extending away from the handle portion.

19. The device of any one of clauses 1-15, wherein the at least one lever surface is a rotational lever configured to rotate the applicator cap about a central axis of the container in a first direction.

20. The device of any one of clauses 1-15, or 19, wherein the handle portion comprises a helical first surface and a helical second surface opposite and spaced apart from the helical first surface.

21. The device of any one of clauses 19 or 20, wherein the container further comprises a handle portion having a first end, a second end, and a body that extends between the first end and the second end, wherein the body comprises at least one lever surface;

wherein the at least one lever surface is a rotational lever configured to rotate the container about a central axis of the applicator cap in a second direction opposite of the first direction.

22. The device of clauses 21, wherein the handle portion of the container comprises a helical first surface and a helical second surface opposite and spaced apart from the helical first surface.

23. The device of clauses 21, wherein the handle portion of the applicator cap, and the handle portion of the container, are each configured to provide rotational forces opposite each other.

24. The device of any one of clauses 21-23, wherein the container comprises a concave surface that defines the reservoir.

25. A method of applying a contact lens to a wearer's eye the contact lens stored in a package comprising an applicator cap comprising a handle portion having a first end, a second end, and a body that extends between the first end and the second end, wherein the body comprises at least one lever surface; and a container having a reservoir configured to house a contact lens and packaging solution, wherein the at least one lever surface is configured to provide at least one leverage point for movement of the applicator cap relative to the container, and wherein the second end is configured to form a seal against a convex surface of the contact lens, the method comprising:

rotating the handle portion with the leverage point;

breaking the seal between the convex surface of the contact lens and the second end of the applicator cap;

removing a contact lens from the convex surface; and applying the contact lens to the wearer's eye.

26. The method of clauses 25, wherein rotating the handle portion further comprises rotating the handle portion about an edge of the container.

27. The method of clauses 25 or 26, wherein rotating the handle portion further comprises rotating the handle portion about a central axis of the container.

25. A method of packaging a contact lens, comprising:

providing packaging solution in a container;

providing a cap with a convex surface that is sealable with the container;

providing a contact lens in a convex up orientation in the convex surface forming a seal; and sealing the container by pressing the lid to the container.

Not all the features described herein need to be incorporated into every package, and those of skill in the art, using the teachings herein, can combine the features to provide a wide variety of improved contact lens packages. In summary, the contact lens packages of the present invention incorporate several novel functionalities which may be combined in a wide variety of combinations as described herein to provide the desired improved and/or single touch packaging. The breadth and scope of the present invention should not be limited by any of the above-described exemplary embodiments but should be defined only in accordance with the following claims and their equivalents.

What is claimed is:

1. A device for storage and application of a contact lens, the device comprising:

an applicator cap comprising a handle portion having a first end, a second end, and a body that extends between the first end and the second end, wherein the body comprises at least one lever surface; and a container having a reservoir configured to house a contact lens and packaging solution, wherein the at least one lever surface is configured to provide at least one leverage point for movement of the applicator cap relative to the container, and wherein the at least one lever surface is a rotational lever configured to rotate the applicator cap about a central axis of the container in a first direction.

2. The device of claim 1, further comprising a seal wrap disposed about the applicator cap and the container, wherein the seal wrap is configured to secure the applicator cap and the container together.

3. The device of claim 1, wherein the container comprises at least one seal surface, and wherein the at least one seal surface of the container abuts the applicator cap when the device is in a closed configuration.

4. The device of claim 1, wherein the container comprises at least one seal surface, wherein the at least one seal surface of the container comprises a tapered surface that tapers away from the handle portion.

5. The device of claim 1, wherein the container comprises at least one seal surface, wherein the at least one seal surface of the container further comprises threads configured to engage with corresponding grooves of the applicator cap.

6. The device of claim 1, wherein the container comprises at least one seal surface, wherein the at least one seal surface of the container comprises a plurality of concentric circular seals.

7. The device of claim 1, wherein the container comprises polypropylene.

8. The device of claim 1, wherein the applicator cap comprises a convex surface opposite and spaced apart from the handle.

9. The device of claim 8, wherein the applicator cap further comprises a plurality of fins that define a plurality of reservoir channels in the convex surface of the applicator cap, and wherein the reservoir channels are configured to retain packaging solution.

10. The device of claim 8, wherein the applicator cap comprises at least one seal surface, and wherein the at least one seal surface of the applicator cap abuts the container when the device is in a closed configuration.

11. The device of claim 8, wherein the applicator cap comprises at least one seal surface, and wherein the at least one seal surface of the applicator cap comprises a plurality of concentric circular seals.

12. The device of claim 8, wherein the applicator cap comprises at least one seal surface, and wherein the at least one seal surface of the applicator cap comprises threads configured to engage with corresponding grooves of the container.

13. The device of claim 8, wherein the applicator cap comprises at least one seal surface, and wherein the at least one seal surface of the applicator cap is configured to fluidically seal against the container.

14. The device of claim 1, wherein the applicator cap comprises polypropylene.

15. The device of claim 1, wherein the applicator cap and the container are made of a uniform material.

16. The device of claim 1, wherein the at least one lever surface is configured to rotate the applicator cap about an edge of the container.

17. The device of claim 1, wherein the handle portion comprises a curved first surface, and a curved second surface opposite and spaced apart from the first curved surface, one of the first and second curved surfaces defining a finger receiver.

18. The device of claim 16, wherein the applicator cap further comprises a dimple extending away from the handle portion.

19. The device of claim 1, wherein the handle portion comprises a helical first surface and a helical second surface opposite and spaced apart from the helical first surface.

20. The device of claim 1, wherein the container further comprises a handle portion having a first end, a second end, and a body that extends between the first end and the second end, wherein the body comprises at least one lever surface;

wherein the at least one lever surface is a rotational lever configured to rotate the container about a central axis of the applicator cap in a second direction opposite of the first direction.

21. The device of claim 20, wherein the handle portion of the container comprises a helical first surface and a helical second surface opposite and spaced apart from the helical first surface.

22. The device of claim 20, wherein the handle portion of the applicator cap, and the handle portion of the container, are each configured to provide rotational forces opposite each other.

23. The device of claim 1, wherein the container comprises a concave surface that defines the reservoir.

24. A method of applying a contact lens to a wearer's eye the contact lens stored in a package comprising an applicator cap comprising a handle portion having a first end, a second end, and a body that extends between the first end and the second end, wherein the body comprises at least one lever surface, wherein the at least one lever surface is a rotational lever configured to rotate the applicator cap about a central axis of a container in a first direction; and a container having a reservoir configured to house a contact lens and packaging solution, wherein the at least one lever surface is configured to provide at least one leverage point for movement of the applicator cap relative to the container, and wherein the second end is configured to form a seal against a convex surface of the contact lens, the method comprising:

rotating the handle portion with the leverage point about the central axis of the container;

breaking the seal between the convex surface of the contact lens and the second end of the applicator cap;

removing a contact lens from the convex surface; and applying the contact lens to the wearer's eye.

25. The method of claim 24, wherein rotating the handle portion further comprises rotating the handle portion about an edge of the container.

26. The method of claim 24, wherein rotating the handle portion further comprises rotating the handle portion about a central axis of the container.

27. A method of packaging a contact lens, comprising:

providing packaging solution in a container;

providing a cap with a convex surface that is sealable with the container, wherein the cap comprises a handle portion having a body that includes at least one lever surface, wherein the at least one lever surface is a rotational lever configured to rotate the cap about a central axis of the container;

providing a contact lens in a convex up orientation in the convex surface forming a seal between the convex surface of the cap and a concave surface of the contact lens; and sealing the container by pressing the cap to the container.

* * * * *